United States Patent
Mady

(10) Patent No.: US 8,021,854 B2
(45) Date of Patent: Sep. 20, 2011

(54) METHOD OF TREATING VASCULAR DISEASE

(76) Inventor: Attila Mady, Santa Rosa, CA (US)

( * ) Notice: Subject to any disclaimer, the term of this patent is extended or adjusted under 35 U.S.C. 154(b) by 0 days.

(21) Appl. No.: 12/724,602

(22) Filed: Mar. 16, 2010

(65) Prior Publication Data

US 2010/0197707 A1   Aug. 5, 2010

Related U.S. Application Data

(63) Continuation-in-part of application No. 11/868,393, filed on Oct. 5, 2007, now abandoned.

(51) Int. Cl.
*C12Q 1/56* (2006.01)
(52) U.S. Cl. ......................................................... 435/13
(58) Field of Classification Search ...................... 435/13
See application file for complete search history.

(56) References Cited

U.S. PATENT DOCUMENTS

| 4,847,276 | A | 7/1989 | Yarrington |
| 6,103,740 | A | 8/2000 | Lakshmanan |
| 6,376,242 | B1 | 4/2002 | Hanson |
| 6,585,995 | B1 | 7/2003 | Hanson |
| 7,022,521 | B2 | 4/2006 | Hanson |
| 7,192,914 | B1 | 3/2007 | Marth et al. |
| 7,723,064 | B2 * | 5/2010 | Chapman-Montgomery et al. ............................. 435/13 |
| 2004/0038997 | A1 * | 2/2004 | Macey ..................... 514/263.34 |
| 2004/0087486 | A1 | 5/2004 | Hanson |
| 2005/0228001 | A1 | 10/2005 | Hanson |
| 2008/0113024 | A1 | 5/2008 | Hanson |
| 2010/0008913 | A1 | 1/2010 | Hanson |

OTHER PUBLICATIONS

Endler G. et al. Mean Platelet Volume is an Indepdent Risk Factor for Myocardial Infarction but Not for Coronary Artery Disease. British J of Haematology 2002, 117, 399-404.*
Kennon S. et al. The Central Role of Platelet Activation in Determining the Severity of Acute Coronary Syndromes. Heart 2003 89:1253-4.*

* cited by examiner

*Primary Examiner* — Ralph Gitomer

(57) ABSTRACT

A method for attenuating the incidence and severity of endovascular disease, arrhythmias and malignancy via a reduction in the total circulating platelet volume is presented. The method will achieve the reduced rates of acute coronary syndromes observed in patients with essential thrombocytopenia and will overcome the shortcomings of current anti-platelet therapies that fail to recognize that the mere presence of platelets above certain threshold concentrations is injurious to the endothelium. This method may include pharmacologic platelet inhibition and anticoagulation prior to mechanical or pharmacologic reduction of platelet counts and total circulating platelet volume and does not permit any transient increase in the total circulating platelet activity, or a transient or permanent increase in the total number of platelets, activated platelets, immature platelets or platelet precursor cells in the peripheral circulation.

18 Claims, No Drawings

METHOD OF TREATING VASCULAR DISEASE

This application is a CIP of application Ser. No. 11/868,393 filed Oct. 5, 2007, now abandoned.

TECHNICAL FIELD

Present invention relates to health, cardiovascular disease and medical therapy.

BACKGROUND OF THE INVENTION

Cardiac and vascular disease, most prominent among them atherosclerosis, have emerged as the number one killer of modern man. In the search for the central causative factor for this scourge of modern man, cholesterol quickly rose to prominence.

From the very outset of atherosclerosis research, it has simply been assumed that endovascular (i.e.: blood component) factors are responsible for the genesis of both micro and macrovascular disease. In other words, intrinsic characteristics of the vascular endothelium and wall were assumed to be secondary in the genesis of vascular pathology of all causes, whether atherosclerotic, inflammatory or other. The one credible challenge to this assumption would appear to be nitrates' ability to ameliorate the effects of atherosclerosis (nitrates act predominantly in the vessel wall and, through release of Nitric Oxide, cause dilation of arteries and arterioles). However, while there is anecdotal and clinical evidence that nitrate-related vasodilation does indeed attenuate the severity of symptoms related to atherosclerosis, there is no evidence to suggest that nitrates have any effect on the genesis or progression of the atherosclerotic lesions themselves (experiments conducted on diabetics showed impaired arterial dilation at early stages of the disease, but no causal connection of this phenomenon to atherosclerosis has ever been proven).

As shall be demonstrated through the course of the discussion that follows, the absence of any clinical or laboratory evidence regarding innate pathology of the vascular wall, as well as the absence of any effective therapies targeted at the vascular wall itself thus supports the thesis that diseases of the vascular wall are primarily a result of insults that are extrinsic to the vascular wall itself. These facts, coupled with the observation that significant atherosclerosis is essentially non-existent in primitive cultures even in individuals of advanced age, justifies the inference that characteristics intrinsic to the vascular wall play a far secondary, if any, role in the pathogenesis and progression of atherosclerosis.

It would then appear that res ipsa loquitur when it comes to environmental and behavioral factors operating through humoral mediators as the predominant cause of atherovascular disease. The same, however, cannot be said for cholesterol as the cause of atherosclerosis and its sequelae. Though extraordinary resources have been devoted to cholesterol by public health agencies and the pharmaceutical industry to the point where this vision rules supreme in the public consciousness almost to the exclusion of any other possibility, the evidence in support of cholesterol is controversial at best.

The dominance of cholesterol as the designated causative factor in atherosclerosis is an unfortunate reality that has not only led to a squandering of resources, but also to a vast array of recognized and unrecognized complications due to only partially effective, or outright ineffective treatment regimes. All of the statins, for example, required serial clinical trials to demonstrate any clinical efficacy; yet, in spite of only tenuous evidence regarding their efficacy and their known significant side effect profile (statins cause overt severe side effects such as hepatitis and myositis, as well as more insidious cognitive loss and erectile problems due to their complex effects on cholesterol metabolism), cholesterol-targeting drugs consistently occupy top positions in the list of most-prescribed (and most profitable) drugs.

Considering the lack of efficacy and poor risk-reward profile of cholesterol-related interventions, it is puzzling why cholesterol should have become so prominent a rallying cry; after all, the oft misquoted Framingham Study, along with numerous subsequent follow-up cohorts such as the Physician's Health Study, the British NHANES and numerous other investigations worldwide have demonstrated clearly that any association between cholesterol and cardiac disease is statistical at best, and less important than hypertension, for instance.

The current "war on cholesterol" rests on pioneering (and deeply flawed) studies by Ancel Keys, PhD, as well as subsequent tissue studies noting the presence of cholesterol in "foam cells" found within the walls of damaged blood vessels. It was then theorized—though never studied or conclusively proven—that these "foam cells" originate from myocyte precursors that somehow decide to begin "sucking out" cholesterol from the bloodstream and thus swell to become "foam cells". These cells, in turn, are purported to release fatty acid precursors when they die and deteriorate. The released fatty acid then causes more local inflammation, which produces more damaged myocytes susceptible to the influence of cholesterol and thus propagates the initial insult. Periodically these damaged myocytes then "heap-up" and the cap of this "plaque" ruptures, exposing a surface that attracts platelets and causes an intra-vascular "plug"—a "vaso-occlusive crisis".

In spite of the clear and convincing evidence contradicting this theory, (ÁRSÆLL JÓNSSON, BJARNI A. AGNARSSON and JÓNAS HALLGRÍMSSON, "CORONARY ATHEROSCLEROSIS AND MYOCARDIAL INFARCTION IN NONAGENARIANS: A RETROSPECTIVE AUTOPSY STUDY, Age and Ageing, Volume 14, Number 2, Pp. 109-112), tens of billions of dollars have been devoted annually worldwide to popularizing and marketing the urban legend of a sudden intra-vascular luminal obstruction arising out of a spontaneous, insidious and inexorable process of lipid deposition. In addition to the aforementioned stranglehold on the pharma best-seller charts, cholesterol also dominates the invasive cardiovascular (and CNS and peripheral vascular) market in terms procedures built around its management. In fact, two prominent medical subspecialties—interventional cardiology and (cardio)vascular surgery—have been built exclusively based the concept of "relieving atherosclerotic obstructions".

Rather than a scientific basis, the key to the popularity of the cholesterol hypothesis lies in its visual—and visceral—impact. The sophisticated graphics splayed all over the media to sell this concept are particularly effective because of fats' linkage to bile secretion and the ability of out-of-context visual images of fat to induce nausea when not accompanied by the aroma of actual food. The "cholesterol blockage" is drawn in exquisite, greasy detail with nauseating little droplets of fat dripping through it. We are told that opening this "blockage" would somehow relieve an "obstruction"; this resonates with human nature, which is interferential. People want the matter "taken care of" and the most demonstrably interferential the "treatment", the more satisfying the "cure". What more satisfying, therefore, then relieving a "blockage"?

Yet cholesterol metabolism disarray as the exclusive causative factor in the genesis of cardiac and vascular disease is untenable. Cholesterol as the main culprit not only runs contrary to common sense in terms of ignoring the presence of a robust barrier—the endothelium—to the initiation of this disease cycle, but it also faces an increasing body of scientific and statistical evidence contradicting it. After decades of exhaustive research, the mechanism whereby cholesterol would initiate and then propagate vascular injury within the blood vessel remains elusive. In fact, the cholesterol/atherosclerosis data cycle has undergone so many iterations that most scientists and practitioners now view with cynicism the arrival of the newest "latest and best" data. Cholesterol drugs (except for niacin, the original and still most effective intervention in this respect) have required so many "studies" and "statistical revisions" to show any effect whatsoever that the original data has effectively disappeared in the process.

Even more damning, the emergence of today's very effective cholesterol reducing drugs has had a paradoxical derogatory effect on the reputation of cholesterol as the arch-villain. Now that statins, as well as modulators specific to just about every subsegment of the cholesterol/triglyceride continuum have become available, precise and strict control of cholesterol levels has become possible in even the most dyslipidemic patient. Yet the predicted dramatic benefits in terms of reduction of morbidity and mortality have failed to materialize and repeated studies attempting to demonstrate regression of plaque upon strict control of cholesterol have proven an utter failure. (Some IVUS—Intravascular Ultrasound—based studies claimed to demonstrate plaque regression on the order of 1 to 2 percent over a period of 24 or so months; these results were claimed to be not only statistically significant, but downright "dramatic", even though the population cohorts of these studies were small (on the order of 100 to 200 patients) and within the measurement variability for IVUS).

Most problematic of all is the fact that "bad cholesterol" makes zero sense from an ontological perspective. Cholesterol's claim to being the progenitor of atherosclerosis would be immeasurably strengthened if someone came up with even the slightest Darwinistic survival advantage to elevated LDL cholesterol, yet no one has been able to divine such an advantage.

This is in direct contrast to platelets, whose complex and difficult role in homeostasis mandates a direct and dramatic downside in terms of vascular patency. A downside so dramatic, in fact, that even animals seem to be aware of it, as various species have been observed to chew on willow bark in spit of its bitter and unpalatable taste.

It is commonly accepted that willow bark's medicinal properties were originally discovered by primitive cultures by observing this animal behavior. It was initially theorized animals gravitated towards this medicine because willow bark's anti-inflammatory effects. However, there is an alternative possibility: while salicin (the primary anti-inflammatory in willow bark) itself is not considered to have strong anti-platelet properties, willow bark does contain other compounds that do. Could it be that at least in part animals chew on this bark to regulate their clotting and platelet thermostat and that this in some way does confer sufficient Darwinistic survival advantage to promote those individuals that do have this habit? (Some species of animals will also root out onion bulbs in nature, even in the middle of winter. Wild onions are not sweet and there appears to be no other cause than medicinal properties to seek them out).

The possibility exists that many species have platelet counts with pathologic vascular consequences in the long term. These effects are irrelevant in nature, however, because most animals don't live long enough to see these negative consequences (and also because many species simply don't have large enough arteries to experience turbulent flow). Even when it comes to human beings, while homo sapiens developed the genetic capacity for a relatively long life span in prehistoric times, trauma and infection remained by far the most important mechanisms of demise throughout known human history. Life expectancies did not exceed the three decade mark in many societies until the mid $19^{th}$ century and continues to hover around this figure in several undeveloped nations today (Swaziland, Mozambique, Zambia, Sierra Leone. Source: United Nations, CIA World Factbook, etc.).

It follows from the above that the survival impact of rapid and effective hemostasis in nature far outweighs any possible increases in the incidence of intravascular events caused by high platelet counts. Further, it is logical to assume that if the coagulation cascade and hemostasis apparatus can be demonstrated to be a participant in the development of vascular disease—which they are known to be—then it is irrefutable that the survival traits of rapid hemostasis are in direct conflict with the requirements of long term vascular patency. In other words, there is a "coagulation and hemostasis thermostat", which thermostat has been set to maximum rapidity and efficacy, at the expense of optimal blood vessel patency.

Which brings us to platelets and the expression "Everything old is new again." As far back as 1950—far before cholesterol was considered anything but a steroid precursor—Dr. Lawrence L. Craven, MD noticed that aspirin inhibited platelet function and that it also dramatically reduced cardiovascular events. Platelets then instantly shot to the forefront in the selection process of a cause for atherosclerosis. For various reasons, however, platelets fell by the wayside in the competition with cholesterol as the primary candidate for investigation.

The first and foremost reason why the platelet theory of atherosclerosis lost its initial momentum was simple economics: it is exceedingly difficult to derive profit from a commonly available and very inexpensive remedy such as aspirin. Nevertheless, as shall be discussed later, there were also some truly confounding studies that did justifiably challenge platelets' role in atherogenesis. Which doesn't negate the vast body direct and indirect evidence that demonstrates that abandoning this original line of thought was a grave mistake.

While aspirin can admittedly lead to dangerous bleeding, tracing the atherosclerosis back to the platelet itself would have led investigators to consider the option of eliminating even aspirin from the equation. Yet it appears that simple mechanical or pharmacologic reduction of platelet counts (with some caveats, as shall be outlined later—what is really meant here is reduction in total platelet activity, for which platelet counts may serve as a surrogate index under some circumstances) is a treatment option that has never been seriously investigated. Which is surprising, since—unlike as it is the case with aspirin—it is known that platelet counts as low as 50,000 per microliter confer no additional risk of bleeding (as long as the platelets present are normal in morphology and function).

If the medical research industry were indeed unbiased, never mind actually efficient, the least that should have happened at some point was that at least a single researcher should have raised the possibility of reducing platelet counts (with or without aspirin as an adjutant) as a treatment alternative. Logic dictates that even in the absence of the unique observations of the applicant of this patent (confirmed by multiple cardiovascular colleagues) that patients with chronic platelet counts significantly below normal exhibit neither acute, nor chronic endovascular disease, at least one prominent researcher should have sought to mimic the effects of aspirin through a different means, if for no other purpose than to further elucidate the mechanism of its function.

Instead, we now know a lot about aspirin's mode of action without any attempts to enhance its effects or improve its safety profile. There are now copycat drugs available that are less effective and less safe. And, though we know that the primary mode of failure of aspirin is acetylation-resistance, and we also know that a significant proportion of patients are therefore resistant to aspirin's anti-platelet effects, almost nobody in clinical practice gets tested for such resistance.

Similarly, one of the fundamental tenets of basic logic (first stated by Aristotle) is that if the opposite of a statement is untrue, than the statement must be true. Applying this principle to platelets, the corollary to the observation that patients with essential thrombocytopenia do not develop endovascular disease is the undeniable fact that ALL hemodialysis patients (even those with very low cholesterol) inevitably develop horrendous and widespread atherosclerosis after a very short time on this treatment.

While hemodialysis lowers platelet counts, it is because dialysis activates platelets; this also releases platelet-related mediators. Suprisingly, small scale studies indicate that the rates of atherosclerosis and peripheral vascular disease are similar in patients who are dialyzed peritoneally. This observation makes perfect sense, however, once we consider that PD patients also suffer from elevated Blood Urea Nitrogen (BUN) and uric acid rendering their platelet function abnormal, while retaining more platelets to produce direct intravascular injury as compared with HD (hemodialysis) patients.

It is fascinating to note that GOUT is also known to pose a significant (though little discussed) cardiovascular risk. This risk, which is much higher than that posed by even dramatically elevated cholesterol levels, not only ties in with the above observation about PD and HD, but also with the article by Miha Furlan, Ph.D., Rodolfo Robles, Miriam Galbusera, Sc.D., Giuseppe Remuzzi, M.D., Paul A. Kyrle, M.D., Brigitte Brenner, Manuela Krause, M.D., Inge Scharrer, M.D., Volker Aumann, M.D., Uwe Mittler, M.D., Max Solenthaler, M.D., and Bernhard Lämmle, M.D., entitled "Von Willebrand Factor-Cleaving Protease in Thrombotic Thrombocytopenic Purpura and the Hemolytic-Uremic Syndrome" and published in Nov. 26, 1998 in The New England Journal of Medicine, (No. 22, 339:1578-1584) (this issue shall be discussed further in the Prior Art and Detailed Description of the Invention).

As shall be discussed later, this observation that in high uremic states von Willebrand factor may be dysfunctional and that HD and PD patients thus have comparable rates of atherosclerosis not only further strengthens the case for the pathogenicity of platelets, but also emphasizes that platelet count and total body platelet activity are not synonyms and must be separated in any proposed treatment regime (though they can converge temporarily, such as in the steady state of platelet reduction, in which case platelet counts can serve as a surrogate measurement for total body platelet activity).

Indeed, defective processing of von Willebrand polymers due to any cause leads to increased platelet aggregation and activation and thus vascular disease, as will be discussed in the Prior Art. Based on this evidence, reduction of von Willebrand levels is prescribed by U.S. Pat. No. 7,192,914. This concept is based on Valentin Fuster and E. J. Walter Bowie's animal studies entitled "Von Willebrand's disease in pigs and atherosclerosis", published October 1979 in the International Journal of Clinical & Laboratory Research. The above cited study found that in the pig animal model von Willebrand's disease (i.e.: a deficiency of von Willebrand factor) is protective of atherosclerosis. This conclusion was bolstered by the observation by Frank W. G. Leebeek, MD, PhD, Irene M. van der Meer, MD, PhD and Jacqueline C. M. Witteman, PhD in their article entitled "Genetic Variability of von Willebrand Factor and Atherosclerosis", published 2004 in Circulation (110:e57) that increased levels of von Willebrand factor are associated with an increased incidence of atherosclerosis. An exact mechanism for this finding has neither been postulated, nor proved, but is not unexpected given that von Willebrand factor not only has a role in coagulation, but also platelet aggregation and activation. Which suggests that this "von Willebrand effect" is secondary to this agent's effects on platelets (and the disease is thus better treated by going straight to the cause).

Proceeding along the chain of evidence of platelet activation, Glanzmann's thrombasthenia is a genetic dysfunction of the IIb/IIIa receptor that prevents platelet activation. Glanzmann's would appear to present a perfect real-life laboratory to study platelets as a potential causative factor of atherosclerosis. Since patients with Glanzmann's are known to suffer from impaired activation of their platelets, it would seem that having Glanzmann's is tantamount to having a reduction in platelet counts.

Glanzmann's patients were long believed to be exempt from atherosclerosis. This was based on clinical observations that Glanzmann's patients bleed but do not get heart attacks. O. Shpilberg, MD, MPH, I. Rabi, MD, K. Schiller, R. Walden, MD, D. Harats, MD, K. S. Tyrrell, PhD, B. Coller, MD and U. Seligsohn, MD. contest this assumption in their article entitled "Patients With Glanzmann Thrombasthenia Lacking Platelet Glycoprotein $_{IIb}\beta_3$ (GPIIb/IIIa) and $_v\beta_3$ Receptors Are Not Protected From Atherosclerosis", published 2002 in Circulation (105:1044-1048).

Unfortunately, the diminutive sample size—seven patients—is a serious flaw of this study. Glanzmann's patients demonstrate great bleeding and atherosclerosis variability (due to genetic heterogenicity) and such a sample size is not likely to be adequate. Also, there was no pathologic study to follow up the findings (ultrasound is an imprecise diagnostic tool with poor spatial resolution). But the fact that renders this study completely irrelevant is the known fact that Glanzmann's platelet are very much active (just not via the IIb/IIIa mechanism).

Mechanical activation of platelets easily explains how Glanzmann's patients can have atherosclerosis yet be free of ACS. For here it must be emphasized that while the prevailing rates of atherosclerosis in Glanzmann's may be controversial, it is still accepted that rates of cardiovascular events are considerably decreased. At first glance Shpilberg would appear to be in the clear, since he's careful to point out that his intent is not to investigate occlusive events, but rather to test the assumption that "platelets have been suggested to play a role in the early development of atherosclerosis".

Nevertheless, given the fact that mechanical activation is most likely to occur in large caliber vessels (the study measured carotid intima thickness and the carotid is known as a large caliber vessel with turbulent flow leading to mechanical platelet activation), as well as close downstream from embolization sources (the aortic valve and aortic bulb, even more prominent sites of turbulence), this study is shockingly irrelevant in terms of trying to identify Glanzmann's impact on atherosclerosis. Intermediate or low caliber vessels with proven laminar flow should have been used as target sites of this study and thus the only inference to be drawn from the findings is that Glanzmann's does not equate to having no platelets and—once again—that platelet counts and platelet activity are not synonyms.

The review article entitled "Glanzmann's Thrombasthenia", by Alan T. Nurden, published 2006 in Orphanet Journal of Rare Diseases (1: 10) presumes to sum up the status quo regarding Glanzmann's in the following fashion: " . . . Since therapeutic inhibition of platelet αIIbβ3 function prevents arterial thrombosis, patients are empirically protected from this disease. It has been speculated that patients with GT may also be protected from atherosclerotic disease. However, studies within ethnic groups in Israel have suggested that this is not so. Patients with GT also are not protected against venous thrombosis, where plasma coagulation factors are of primary importance." Unfortunately, however, Nurden's conclusions (i.e.: about Glanzmann's providing no protection against atherosclerosis) must be discounted, as the article refers back to the Schpilberg study as its primary proof.

Referring back to the section on hemodialysis, it's easy to understand how mechanical activation renders any biochemical defect completely irrelevant in terms of the atherogenic potential of platelets. And this effect can even extend to the microvasculature—and, thus laminar flow zones—as evidenced by the phenomenon known as "pump head", experienced by cardiovascular bypass ("perfusion") and extra-corporeal membrane oxygenation (ECMO) patients. While the cause of this phenomenon is not known for certain, it has been assumed to be due to activated and microaggregated platelet clusters. It is logical to conclude that the process of hemodialysis activates platelets in a manner similar to the cardiovascular bypass machines—to the extent that most patients need to be heparinized during dialysis just to avoid whole body thrombosis—and that this is the reason why patients on hemodialysis have tremendously accelerated progression of atherosclerosis.

Progressing beyond clinical observations to more rigorous scientific data, hematologic studies have revealed that platelets are the most unstable of all cells in the body. Anatomic and post-mortem studies have noted that the earliest and most severe forms of atherosclerosis in the body occur at sites of maximum turbulence, such as in the aorta at the impact of a jet from a stenotic aortic valve. This mechanism of injury could only be due to intimal susceptibility or some unrecognized platelet effect, as platelets are the only component of blood activated in such turbulent jets. However, if atherosclerosis was really a result of intimal susceptibility (rather than inability to resist platelet erosion forever), then there should be at least a few early lesions in small vessels, on a random basis. Which is not the case.

There's even bench scientific research data to explain some of the mechanisms whereby platelets might in fact be the mediators of even cholesterol-related damage. As a for instance are supplied three references addressing the correlation of megakaryocyte dysfunction in diseases states (specifically, diabetes), the effect of fat ingestion on platelet function and the platelet size (as a marker of platelet activation) as a positive risk for acute myocardial events (i.e.: as a marker of acute endovascular injury), respectively.

More remarkably, scientists are also succeeding in elucidating the detailed mechanisms of modulation that regulate platelets' long term effects on the vascular endothelium. Several factors have been isolated which potentiate platelets' negative effects on the endothelium and the vascular wall. It is known that Angiotensin II in the circulation leads to the upregulation of NF Kappa B (Nuclear Factor Kappa B) and subsequent VCAM (Vascular Cell Adhesion Molecule 1) and PAI-1 (Plasminogen Activation Inhibitor 1) production, both of which enhance the progression of atherosclerosis and even gross vascular deformities such as aneurysms. Similarly, the presence and induction of activated Protein C (APC) complexes also accelerate the progression of atherosclerosis. Genetically manipulated mice with increased PAI-1 expression are reported to show more rapid spontaneous stepwise progression of atherosclerosis, though this is controversial. PAI-1 is a factor that modulates the coagulation cascade and is released from activated platelets.

Endothelin is another factor that modulates platelet function and exhibits a role in the genesis of atherosclerosis. Endothelin inhibits platelet aggregation, but has surprisingly been reported to be elevated in patients with atherosclerosis in an article by C. Thiemermann, G. R. May, C. P. Page, and J. R. Vane entitled "Endothelin-1 inhibits platelet aggregation in vivo: a study with 111indium-labelled platelets, published February 1990 in the British Journal of Pharmacology (99(2): 303-308). On face value, this would suggest that a compound that somehow contributes to the genesis of atherosclerosis does so in spite of the fact that it inhibits platelet activity; unless, of course, endothelin is a reaction to endovascular pathology and an attempt by the body to stem the damage from platelets by inhibiting their aggregation.

There is also proof that platelets are responsible for the progression of endovascular disease. As one would expect based on the fact that a scar is a late response to an injury to which the initial response is platelet activation and a platelet plug, platelets have been conclusively demonstrated to be the primary stimulus for fibroblast growth. Platelet extracts cause visible increase in fibroblast activity; this effect is sufficiently dramatic that it can demonstrated through gross cell culture assays and can be visually observed and quantified. And fibroblasts have been noted to uptake lipids and to integrate surrounding debris into the collagenous matrix they secrete to form the predominant bulk of the scar itself. This makes fibrocytes a much better candidate for the role of agents of vascular decay then the "degenerate" myocytes purported to be the responsible for this phenomenon, since myocytes are not known to uptake lipids in any other area of the body (i.e.: skeletal or smooth muscle cells).

Platelets (and compounds released by platelets) have a similar inflammatory effect on white cells and multiple other blood and vascular components. This fact will explain why an association—but not causal!—has been found between ACS and inflammatory indices such (CRP and ESR).

The central role of platelet function is thus demonstrated by clinical observations, clinical studies and hard science data. What's more, some of this hard science data has been extended into the clinical (or, in this case, post-clinical) realm. Specifically, the above mentioned fibrosing and inflammatory effects have been mapped to the plaques that first arise and are usually most severe at areas of maximum turbulence, such as artery bifurcations, sites of jet impact or in the lumen and near bends or tortuosity of large vessels. In this regard, it should be noted that many elderly patients will have as their only sites of atherosclerosis the aorta distal to a stenotic aortic valve, and/or the carotid distal to the carotid bifurcation. For a detailed discussion, the reader is referred in this matter to the tome Vascular Surgery, by Robert W. Hobson, Samuel E. Wilson and Frank J. Veith, pages 42-48.

It should be noted that at first read even the cited reference appears to contradict the above assertions, namely that the location of plaques proves they're caused by platelets. Specifically, the authors go to great lengths to defend the cholesterol hypothesis by quoting studies claiming plaque regression in monkeys on low cholesterol diets. The authors seek to "debunk" the theory that activation of platelets may be involved in atherosclerotic plaque genesis by claiming that maximum plaque deposition occurs in areas downstream from areas of maximal turbulence, rather than areas of maximum turbulence, per se. Which makes perfect sense once more, as mechanical platelet activation is not instant, and these plaques occur just far enough downstream from the original jet that triggers platelet activation to account for the time delay in activation.

Faulty reasoning has become doctrine because even proponents of the platelet hypothesis have failed to adequately study the science behind these phenomena, though the evidence does exist to deduce the pathophysiology. For instance, we know from studies of hydrodynamics that the Reynolds number determines the nature of flow; we also know from real life studies that transition from laminar to turbulent flow is a hysteresis type of transition within a range from 1900 to 2300. Turbulent streams thus inevitably form a cone with a shifting tail that retains turbulent characteristics for a considerable distance downstream into the laminar zone, tapering from the lower velocity flow at sides of the vessel towards the higher velocity center (where the Reynolds number thus remains higher). And, as mentioned above, we know from studies of platelet function that platelet activation is not instantaneous, but rather occurs on the scale of microseconds, which explains the millimeter to centimeter downstream displacement of atherosclerotic plaques from the point of maximum turbulence (BUT STILL WITHIN AN AREA OF TURBULENCE!!!). This rule is further supported by an exception, namely the inevitable aforementioned post-stenotic aortic plaques associated with aortic valve stenosis. Engineering analysis of the jet from such a valve will show Reynolds numbers an order of magnitude greater than those of local turbulence in secondary vessels. It is the markedly increased kinetic energy of this stream that explains why there is no downstream displacement of this aortic plaque; this increased velocity and kinetic energy of the jet causes the platelets to impact against the vessel wall with such speed that they are mechanically damaged and forced to discharge their contents, rather than be activated by the standard route.

One would think that such a compelling chain of evidence would at least mandate some clinical investigation. Unfortunately, however, the current patent is the first to recognize the above explanation for the physical distribution of atherosclerotic plaques in the human body. Further, the current application (and its precursor) is the first to point to the Glagov phenomenon (asymmetric eccentric centrifugal hypertrophy prior to concentric centripetal intrusion of plaque into the lumen) as further proof of this explanation (see original submission), as the eccentricity of atherosclerotic plaques proves that they are a flow-related phenomenon (in contrast to the metabolic hypothesis, which claims that cholesterol is the causative agent of atherosclerotic plaques, but which—if true—would have to produce symmetric circumferential plaques, since cholesterol is evenly distributed in the blood stream and cholesterol is neither activated, nor mal-distributed by turbulence).

So it is a shameful state of affairs that, aside from the consensus that Aspirin is dramatically effective in the reducing the incidence and severity of cardiovascular events, there appears to be complete apathy regarding the long term role of platelets in the pathogenesis of atherosclerosis. And even when it comes to acute "vaso-occlusive events", there is only one large scale study (Philip Bath, MD, FRCP, Charles Algert, MPH, Neil Chapman, MRCP and Bruce Neal, MRCP (UK), PhD for the PROGRESS Collaborative Group, Association of Mean Platelet Volume With Risk of Stroke Among 3134 Individuals With History of Cerebrovascular Disease. Stroke. 2004; 35:622-626) that sought to examine the role of platelets in the pathogenesis of such events. The study generated little excitement, as it concluded that elevated PLATELET COUNTS from did not cause an excess of strokes over people with normal levels. However, what was found was that elevated aggregate PLATELET VOLUME—i.e.: the estimated total platelet volume within a body—did correlate with the various endpoints for such events analyzed by the study. Which brings us back once more to the caution: platelet counts and platelet activity are not synonyms.

But are platelet volume and platelet activity synonyms? And, if they are, why would they be? Authorities such as Bernd van der Loo, MD and, FRCP, FESC John F. Martin, MD, who in their "Megakaryocytes and platelets in vascular disease" (Bailliere's Clinical Haematology: Megakaryocytes and Platelet disorders, February 1997, Pages 109-123) explain that individual platelet volume is correlated with platelet activation status, since platelets are known to swell once they activate. It thus makes sense that an increased aggregate volume even in the face of normal platelet counts would lead to an increased number of intra-vascular events, as opposed to rote platelet counts which can represent platelet masses of highly variable activity.

Incredibly, there has never been a study conducted into the DECREASE in the incidence of atherosclerosis and intra-vascular events in patients with ESSENTIAL THROMBOCYTOPENIA, or other conditions that would artificially reduce platelet counts without platelet activation (ITP and some forms of HIT; TTP and HELLP activate platelets and cause thrombocytopenia by way of consumption). The lynchpin for this application thus remains the suprising personal and polled peer data regarding the absence of angina, myocardial ischemia and myocardial infarct among patients with essential thrombocytopenia—data not available to anyone else prior to submission of this patent application.

Which brings us to keystone of the argument that platelets cause atherosclerosis (and a whole lot else): the efficacy of aspirin. In this day and age of nanotechnology, heroic medical interventions and two dollar a pill cholesterol marvels, the single most effective intervention in the prevention and treatment of vascular disease remains Acetyl salicylic acid (Aspirin).

Particularly for "vaso-occlusive disease", low doses of aspirin with low incidences of complications (less than 1% incidence of major haemorrhage) result in morbidity and mortality reductions of 45% (Physician's Health Study). This is even more remarkable in the light of the fact that we now know that up to 50% of patients treated with aspirin are "non-responders", meaning genetically resistant or immune to its acetylating effects. Essentially, what this means is that almost all patients who are susceptible to the effects of Aspirin will see a dramatic effect in terms of endovascular morbidity and mortality.

Granted, the above cited study was conducted at a time when most physicians were males and the study population was thus essentially all male. Recent attempts to study exclusive female cohorts have failed to show a similar cardiovascular benefit, though they have demonstrated a clear CVA-reduction effect. Nevertheless, aspirin's effects in males and in symptomatic cardiovascular patients of both sexes have been confirmed repeatedly. Which means that, while atherosclerosis will probably prove to be multifactorial in origin, there is already overwhelming evidence that platelets occupy the central role.

Unlike the crackpot theories the cholesterol industry periodically parades and then debunks, such as chelation therapy, high dose vitamin C, beta-carotene, meditation and hypnosis, properly designed platelet directed interventions stand a very good chance of conquering this very serious disease. Poor dental hygiene and caries might very well have a role, as might the favorite all-purpose villain of twentieth century medicine, "inflammation", and its corollary, "auto-immune disease", but breakdown of the arterial wall cannot occur in the absence of platelet-related damage (except in conditions of inherent vascular wall abnormality, such as Marfan's syndrom and Ehlers-Danlos). Yet more money has been spent by the ADA (American Dental Association) trying to prove that atherosclerosis is related to poor oral hygiene, then by the AHA (American Heart Association) just reiterating the fact that there is clear and incontrovertible proof that atherosclerosis is a direct result of platelet-mediated damage to blood vessel walls.

Which brings us to the logical and simplest solution to what shall indubitably prove to be an exceedingly complex disease: eliminate the culprit. Reduce the number of provoking entities, namely the number of ACTIVATED platelets, available to injure. What's more, benefits of this treatment will likely extend to a number of other pathologies, since atherosclerosis is already proving to be only a small part of a vast continuum of platelet-related damage. There is now evidence to suggest that many conditions previously considered to have no connection to vascular pathology may in fact be a direct result of it. As a for instance, we know now that effect of platelets is not confined to the endovascular lumen. The initial establishment of tumors is not possible without angiogenesis. Thrombin receptors have been proven to have a role in this initial angiogenesis. Platelets have a role in modulation of thrombin receptors. Reduction of platelet activity (and reduction of vascular pathology, such as atherosclerosis) to safe levels might affect thrombin receptor levels.

Similarly, MS—Multiple Sclerosis, formerly a mainstay of the "autoimmune" mania, now also has a proposed vascular mechanism. Alzheimer's mysterious "fibrillary tangles" are also intriguing and would make a whole lot more sense from a vascular/platelet perspective. The list of potential platelet-mediated phenomena is endless, which is why it is so imperative to establish the current evidence and thus provide the foundation for the research necessary to fully explore its implications.

While many of the fundamentals of this treatment are supported by solid evidence, much work does remain. Patients with functional platelet counts down to 50,000 per microliter (i.e.: patients who are not uremic, in DIC, or have no other specific platelet dysfunction) are considered to have no excess bleeding risk based on clinical experience, but there hasn't been a single study to date to examine whether such a reduction is indeed completely safe. Thus, this may prove to be an erroneous assumption once more rigorous investigations are completed. Also, current methods to reduce platelet counts may prove inadequate to the task of reducing the incidence of and treating atherosclerosis and atherosclerosis-related pathology.

But whatever the technical difficulties and however much information is lacking in this area, one thing will be proven beyond a shadow of a doubt through the course of this discussion: platelets are the primary culprit of endovascular disease and their sequelae. While all treatment to date has focused on indirectly modulating their effects, the only foolproof method of ameliorating the harm from unnecessarily high platelet activity is to contain the culprit. Hence, this patent.

Lexicon

Preamble

A lexicon is necessitated by prior art that is self-contradictory and of no clinical utility (as proven by prior clinical studies—see all the studies cited in the body of the Prior Art, Detailed Description of the Invention, as well the IDS). A review of the exact meaning and context of the terms to follow shall not only help to distinguish the current application from the prior art of U.S. Pat. Nos. 6,376,242, 6,585,995 & 7,022,521, but will also clarify existing scientific fact and will thus introduce reason into a very convoluted and disputed discipline.

Further, this Lexicon is also because standard definitions of endovascular disease are not only likely to be incorrect, but have already been proven to be so. As noted in the Background of the Invention, while no new consensus has been established to replace the old terms, the very idea of "atherosclerosis" and "vaso-occlusive" disease has been proven to be deeply flawed and will have to be discarded at some point. We now know beyond doubt that endovascular disease is a continuum of pathologies whose full extent is unknown. In fact, even the term "endovascular disease" is likely to be too limited, since—as has been explained above, in the Background of the Invention—platelet-related disease probably extends deep into tissues outside of the vascular lumen.

So why not just refer to this continuum as "platelet-related disease"? This term, while technically correct, would be too broad and would sever the relationship of the old "atherosclerosis" with endovascular platelet-related disease. This would be unfortunate, since there is a significant amount of readily transferable data developed around this obsolete concept. Distancing platelet-related disease from atherosclerosis too far would result in disposal of sound and relevant scientific information solely on its lack of "trendiness". Total focus on platelets would tempt the scientific community towards another extreme dogma along the lines of "autoimmune disease" and "vaso-occlusive crisis", wherein all vascular disease would be instantly lumped into this wastebasket pigeonhole.

The concept of vascular pathology emphasizes the fact that while we do have ample proof and some rudimentary understanding of the genesis of endovascular pathology, we are far from understanding the exact mechanisms of its progress and we have almost no idea regarding its full ramifications. While this patent will primarily discuss endovascular pathology, because of the vast spectrum of extra-vascular sequelae it shall be understood to apply to vascular disease in general. Rather than being concerned about narrowing down the focus of any potential research, it seeks to encourage researchers to keep their perception open to the possibility that apparently completely unrelated phenomena might in fact have their genesis in the endovascular process initiated by platelet disregulation. Which doesn't mean that platelets should suddenly morph into the new boogie-man. For this reason, the terms to follow shall be defined with careful caveats, as they will likely have to be further modified in the near future.

Definitions

Note: All terms defined herein apply to all species with blood platelets that perform a substantially analogous function to those of human platelets (i.e.: clot formation and hemostasis).

"Candidates at risk" shall include all individuals and populations with any risk of, or incidence of endovascular disease or its sequelae, as long as this endovascular risk outweighs risk of treatment. In other words, even healthy individuals belonging to a subgroup with a reduced rate of endovascular rate as compared to the general population would fall in the category of candidates at risk, as long as treatment morbidity and mortality is significantly exceeded by the risk of morbidity and mortality from endovascular disease and its sequelae. This definition holds regardless of the mechanism of this risk, or its absolute magnitude, as long as treatment can be demonstrated to provide a benefit. Thus, based on presently available data, candidates at risk will include individuals with a history of institutional care, reduced mobility, smoking, oral anti-contraceptive, hormone replacement therapy or testosterone use, elevated platelet counts, obesity, diabetes, elevated cholesterol, elevated lipids, atherosclerosis, peripheral vascular disease, arterial thrombosis, stent thrombosis, coronary graft thrombosis, peripheral bypass graft thrombosis, venous thrombosis, microvascular thrombosis, heart valve thrombosis, arterial emboli, venous emboli, microvascular emboli, arterial stenosis, myocardial infarction, infarction of other organs, transient ischemic attack, stroke, past or prospective angiography, angioplasty, stent, coil or other intravascular appliance placement, coronary, peripheral or CNS bypass surgery, other vascular surgery, other abdominal, peripheral limb or plastic surgery, carotid artery procedures, vascular grafting, thrombectomy, organ transplant, heart transplant, vascular laser therapy, vascular replacement, arrhythmias, congenital cardiac malformations, radiotherapy to the chest, age above a certain pre-determined threshold, Alzheimer's disease and other dementias, select autoimmune diseases including lupus erythematosus and rheumatoid arthritis, genetic or acquired coagulopathies, kidney failure, hemodialysis, or family history of any of the above, or family history of shortened lifespans in the absence of trauma or self-injury. It is important to note that individuals with Atrial Fibrillation and any other cardiac conditions leading to arrhythmias (such as cardiac non-compaction and ARVD—Arrhythmogenic Right Ventricular Dysplasia—to name a few) also belong in this population.

"Vaso-occlusive event" shall retain Hanson's definition: "As used herein, a vaso-occlusive event includes a pathological partial occlusion (including a narrowing) or complete occlusion of a blood vessel, a stent or a vascular graft. A vaso-occlusive event intends to embrace thrombotic or thromboembolic events, and the vascular occlusion disorders or conditions to which they give rise. Thus, a vaso-occlusive event is intended to embrace all vascular occlusive disorders resulting in partial or total vessel occlusion from thrombotic or thromboembolic events, except those that are related to high platelet count due to a hematological proliferative disorder. A thrombotic event as used herein is meant to embrace both a local thrombotic event and a distal thrombotic event (e.g., a thromboembolic event such as for example an embolic stroke). A vaso-occlusive event also includes abnormal blood vessel growth induced by the presence of platelets and the factors they secrete. An example of this latter form of vaso-occlusive event is intimal hyperplasia which results in a narrowing of the blood vessels (i.e., reduction in the diameter of blood vessels either locally or throughout an extended segment of the vessel) due to a hyperproliferation of cells of the intimal layer of the blood vessel wall."

"Vascular disease" includes known and yet to be discovered vascular pathologies initiated by blood components within the endovascular lumen, as long as those conditions are either caused by platelets, primarily initiated by platelets, or in whose pathophysiology platelets are an indispensable factor. "Vascular disease" thus includes the former atherosclerosis (as well as its subset, "vaso-occlusive crisis", or ACS) intimal injury of any nature and etiology and any other vessel wall injury, whether acute or chronic or whether involving large areas or microscopic segments. "Endovascular disease" further includes thrombotic, embolic or other particulate based conditions.

"Sequelae" shall stand for "sequelae of vascular disease" and shall refer to all known and yet to be discovered pathological consequences of vascular disease. Sequelae shall thus include all conditions that affect any components of blood and lymphatic vessels and contribute to harmful consequences, whether such a linkage may be presently recognized or not. As a for instance, should Alzheimer's disease be found to be caused by microvascular emboli and thrombosis, it would thus fall in the category of sequelae. But in any case, while it is understood that this list is not comprehensive, sequelae already include obstruction, embolization, thrombosis, reduced blood flow, inflammation, pain, circulation-based impairment of any body organ, CNS plaque, neurofibrillary deposits on macroscopic or microscopic scale, microvascular pathology, potentiation of metabolic disorders, general ill-described malaise and failure to recover appropriately after stress conditions, cerebrovascular accidents and large vessel or microvascular CNS disease (whether hypertensive, diabetic, or at present unknown etiology). Potential sequelae of vascular disease include all malignancy states, whether overtly perfusion dependent or not, as well as microvascular cardiac and peripheral disease ("Syndrome X"), Burger's disease (endarteritis obliterans), SIRS (systemic inflammatory response syndrome), ITP, HUS/TTP and frank sepsis (with or without attendant tissue acidosis).

Sequelae and vascular disease and its sequelae also includes all pathologic states to which such disease might contribute, whether such linkage may currently be recognized or not. While understood that this list is not comprehensive, such sequelae would include obstruction, embolization, thrombosis, reduced blood flow, inflammatory states, chronic pain and reduced function to any body organs. Sequelae of vascular disease shall further include plaque and neurofibrillary deposits on macroscopic or microscopic scale, microvascular states, potentiation of metabolic disorders, tissue acidosis, as well as general ill-described malaise and failure to recover appropriately after stress conditions. Sequelae of vascular disease shall include a (past, present or future) history of cerebrovascular accidents, macrovascular or microvascular CNS disease, whether it be hypertensive, diabetic, or at present unknown etiology. Potential sequelae of vascular disease are to specifically include all malignancy states, whether overtly perfusion dependent or not. Sequelae of vascular disease are also to be assumed to include microvascular cardiac and peripheral disease ("Syndrome X") and Burger's disease (endarteritis obliterans), as well as Alzheimer's and other microvascular CNS pathology. Additionally, sequelae of vascular disease for the purpose of this patent is include diseases such as ITP and HUS/TTP and their heretofore unrecognized analogues. Finally, sequelae of vascular disease will also include SIRS (systemic inflammatory response syndrome), as well as frank sepsis.

"Safe reduction of platelet activity" means reduction of platelet activity to levels that maintain sufficient clot formation and blood coagulation to avoid an increase in the clinical risk of major bleeding. Safe reduction of platelet activity is accomplished by means other than pathologic processes, whether acute or, otherwise, that would lead to pathologic impairment of coagulation, as well as secondary disturbances of vascular integrity and function dependent on appropriate platelet function. Safe reduction of platelet activity shall further be construed to include any means necessary to reduce or eliminate the presence of activated platelets, immature platelets, or platelet precursors in the peripheral circulation and does not permit even a temporary increase in these activated platelets, immature platelets, or platelet precursors in the peripheral circulation from normal levels. This reduction has to be direct and immediate and cannot proceed through an intermediary increase step. Safe reduction of platelet activity will also avoid producing any platelet-related compounds with detrimental effects on the vascular endothelium, the clotting cascade, or any other tissues or pathologies potentially affected by platelet activity, or substances regulated by platelet activity. NB: HEMODIALYSIS PATIENTS DO NOT MEET THIS SAFE REDUCTION THRESHOLD, EVEN THOUGH SOME CLINCANS CONSIDER THEM TO HAVE "SPONTANEOUSLY REDUCED PLATELETS". THIS IS BECAUSE HD PATIENTS ACTUALLY HAVE AN IATROGENIC PLATELET REDUCTION DUE TO THE DIALYSIS CIRCUITRY AND THEIR REMAINING PLATELETS ARE OF ABNORMAL MORPHOLOGY AND ARE ALSO SUBJECT TO DYSFUNCTION DUE TO UREMIA. IN LATE STAGES OF THIS DISEASE SOME PATIENTS MAY DEVELOP MYELOFIBROSIS AND CONSISTENT PANCYTOPENIA EVEN IN THE ABSENCE OF ACTUAL HEMODIALYSIS, BUT SUCH PATIENTS CONTINUE TO PRODUCE ABNORMAL PLATELETS.

"Adjunct modalities" refer to adjunct modalities of platelet inhibition and platelet function modulation are to include, but not be restricted to, use of acetyl salicylic acid, clopidogrel, persantine, EDTA, selective filters, irradiation, immunologic and chimeric immunologic therapeutics, IIb/IIIa inhibitors, acute thrombolytic agents, heparin, low molecular heparin, bivalarudin, hirudin, as well as less commonly used anti-platelet and/or anti-coagulant compounds, such as Allium extracts, into therapy and any other agents or interventions which have already been developed, or may be developed during the life of this patent, to have acute or chronic effects on platelet function and coagulation.

CNS—Central Nervous System.

Prior Art

U.S. Pat. Nos. 6,376,242, 6,585,995 & 7,022,521 and USPTO publications 20100008913, 20080113024, 20050228001 and 20040087486 (all by Stephen R. Hanson) are the only relevant prior art to this application. These items refer to the use of "MPL pathway inhibitors", "non-MPL pathway inhibitors" and anagrelide in acute "vaso-occlusive crisis", defined as follows: "As used herein, a vaso-occlusive event includes a pathological partial occlusion (including a narrowing) or complete occlusion of a blood vessel, a stent or a vascular graft. A vaso-occlusive event intends to embrace thrombotic or thromboembolic events, and the vascular occlusion disorders or conditions to which they give rise. Thus, a vaso-occlusive event is intended to embrace all vascular occlusive disorders resulting in partial or total vessel occlusion from thrombotic or thromboembolic events, except those that are related to high platelet count due to a hematological proliferative disorder. A thrombotic event as used herein is meant to embrace both a local thrombotic event and a distal thrombotic event (e.g., a thromboembolic event such as for example an embolic stroke). A vaso-occlusive event also includes abnormal blood vessel growth induced by the presence of platelets and the factors they secrete. An example of this latter form of vaso-occlusive event is intimal hyperplasia which results in a narrowing of the blood vessels (i.e., reduction in the diameter of blood vessels either locally or throughout an extended segment of the vessel) due to a hyperproliferation of cells of the intimal layer of the blood vessel wall."

The Hanson patents (and publications) together constitute a peculiar and confusing meshwork of interdigitating claims that generally aim to reduce platelet counts and thus "inhibit" "vaso-occlusive" episodes through various means. A brief summary of these patents is as follows:

U.S. Pat. No. 6,376,242 proposes to inhibit and treat "vaso-occlusive events" with an MPL-pathway inhibitor. Claim 16 suggests administering this treatment in combination with an "agent to treat vascular disorder or vascular complications".

U.S. Pat. No. 6,585,995 proposes to inhibit and treat "vaso-occlusive events" with a non-MPL-pathway inhibitor. Claim 13 proposes to apply the treatment when " . . . the subject is otherwise free of symptoms calling for treatment with the agent . . . " and claim 14 " . . . when the subject is apparently healthy . . . . "

U.S. Pat. No. 7,022,521 proposes to inhibit and treat "vaso-occlusive events" with anagrelide.

The key points in these patents are "reduction of platelet counts", "vaso-occlusive event" and inhibit. All of the above cited patents and USPTO publications propose in their broadest scope to attenuate the incidence and severity of "vaso-occlusive events" through pharmacological means. As noted above, the definition of a "vaso-occlusive event" is concrete and specific: a thrombotic or embolic event, or a luminal narrowing of a blood vessel. By definition, occlusion of the vessel (partial or total) must be present.

One can argue that these patents are confusing, as they prescribe a vast array of possible interventions that are at times contradictory and at other times nonsensical. The dependent claims are even more puzzling, unless they are deliberately intended to confuse. They appear to add nothing to the claims other than restrict their scope. Claim 16 of U.S. Pat. No. 6,376,242 is one of the few that makes sense, as it proposes adding an "agent to treat vascular disorder or vascular complications". Presumably this would include platelet and/or clotting modulators, as this is implied in the Specification: " . . . The agent of the invention can be administered simultaneously or consecutively with another therapeutic compound such as an agent which would normally be indicated for the subject. Such agents include agents for treating vascular disease or vascular complications (i.e., complications resulting from such disease). In some important embodiments, the agent for treating vascular disease or vascular complications is an anti-thrombotic agent. The anti-thrombotic agent may be selected from the group consisting of an anti-coagulant agent, a fibrinolytic agent and an inhibitor of platelet function, but is not so limited. Thus, in one embodiment, the agent is administered with an inhibitor of platelet function. The inhibitor of platelet function may be selected from the group consisting of aspirin, abciximab, clopidogrel and dipyridamole. In another embodiment, the agent may be administered with an anti-coagulant agent. The anti-coagulant may be selected from the group consisting of glycosaminoglycans (e.g., heparins) and vitamin K antagonists. In a further embodiment, the agent is administered with a fibrinolytic agent, such as but not limited to one selected from the group consisting of plasminogen activators such as tissue plasminogen activator (TPA), streptokinase and urokinase, plasmin and plasminogen. Depending upon the embodiment, the agent of the invention may be administered before, simultaneously with or following administration of the agent for treating vascular disease or vascular complications . . . . "

" . . . Other useful categories of such agents include but are not limited to anti-inflammatory agents, anti-platelet agents, lipid reducing agents, direct thrombin inhibitors, glycoprotein IIb/IIIa receptor inhibitors, agents that bind to cellular adhesion molecules and inhibit the ability of white blood cells to attach to such molecules, calcium channel blockers, beta-adrenergic receptor blockers, cyclooxygenase-2 inhibitors, and angiotensin system inhibitors . . . In any case, it is clear that pharmacologic means are proposed, but this claim was also pointless, since this modality was subsumed by the scope of the independent claim.

What is unequivocal, however, is that Hanson's "vaso-occlusive event" excludes the vast majority of vasculopaths due to the Glagov phenomenon. The Glagov phenomenon states that vessels initially remodel concentrically, meaning expanding outwards from the center and preserving luminal anatomy. For this reason the phrase "intimal hyperplasia" also is unduly restricted (and therefore rendered clinically useless) by the claims of the patent, as most initial remodeling occurs behind the intima and in many cases with only limited disruption of the intima.

Belaboring the deficiencies of Hanson's "vaso-occlusive event" is not just idle hairsplitting. We know now that myocardial ischemia is of multiple etiologies and only a small subset of the clinical phenomena lumped into the Acute Coronary Crisis (ACS) rubric are caused by the classical "vaso-occlusive" phenomenon (wherein a fresh thrombus acutely obstructs the lumen of a blood vessel). Further mechanisms include vasospasm, dissection, long segment atrophy without a focal stenosis with secondary slow obstruction producing critical stenosis under demand, thromboxane-mediated vasoconstriction in response to a partial blockage, false ischemia such as Takotsubo cardiomyopathy, malignant primary arrhythmias related to ion-channel abnormalities, as well as other phenomena that compromise oxygen and nutrient delivery to cardiac tissue in the face of constant or increased metabolic demand. (Interestingly, anagrelide has been associated with Takotsubo. See: Proietti, Riccardo; Rognoni, Andrea; Ardizzone, Fabio; Maccio, Sergio; Santagostino, Alberto; Rognoni, Giorgio. In their "Atypical Takotsubo syndrome during anagrelide therapy", published July 2009 in the Journal of Cardiovascular Medicine, Volume 10-Issue 7-p 546-549).

In fact, most of unstable angina is caused by vasospasm type phenomena, rather than occlusive disease per se, as demonstrated by Yoshiki Yui, Keiji Sakaguchi, Takashi Susawa, Ryuchi Hattori, Yishiki Takatsu, Natsuko Yui and Chuichi Kawai in their "Thromboxane $A_2$ analogue induced coronary artery vasoconstriction in the rabbit.", published in Cardiovascular Research, 1987 21(2):119-123. (Coincidentally, this is also the mechanism whereby the COX-2 inhibitors are believed to cause an increase in heart attacks, as they shift the cyclooxygenase—COX—enzyme towards producing more thromboxane and less bradykinin, thus causing coronary artery vasospasm). For this reason the current technology rejects the concept of "vaso-occlusive crisis", and reverts instead to "hard" science such as physics, chemistry and biochemistry, as well as irrefutable and uncontested anatomic observations.

As will be seen, the evidence supporting the current application invalidates the theatrical and histrionic model of a thrombus occlusion as the sole source of acute cardiac injury and proves it to be a wastebasket default for the wide array of the real life situations that together cause cardiac injury and functional compromise. Additionally, the current technology also rejects the clearly erroneous model of cholesterol as the central etiologic agent for ischemia advanced by drug companies and the current research status quo, replacing it with a model with an extensive array of direct and indirect supporting evidence.

The Hanson patents are not only oblivious regarding these subtleties, they also demonstrate complete ignorance of the difficulties of identifying individuals suffering from "vaso-occlusive events", much less "patients at risk" who "may appear healthy".

The Hanson patents demonstrate complete ignorance regarding the greatest difficulty in cardiovascular medicine, namely the complexity of accurate patient triage for specific treatments and interventions. This triage is an overall probability and severity estimate of future negative outcomes and integrates historic, behavioral and genetic, as well as (hopefully objective) anatomic, physiologic and functional testing information. Hanson gets even more confusing when completely sidesteps these issues and recommends treatment when " . . . the subject is otherwise free of symptoms calling for treatment with the agent . . . " and " . . . when the subject is apparently healthy . . . . " Extraordinary resources are invested into the construction and execution of massive trials for the purpose of elucidating appropriate sub-stratification of candidates for applicable potential treatment modalities. This is because it has been found that blanket application of today's potent medicines and interventions is likely to be of neutral outcome at best, particularly in the chronic setting. It is known that particular care must be exercised when it comes to initiation of therapy in the setting of asymptomatic endovascular disease. Interference in asymptomatic disease states with any but the most indolent treatment modalities has consistently resulted in negative outcomes. Ignoring the need to risk stratify potential treatment candidates makes the proposed treatment nonsensical.

Our understanding of the Glagov phenomenon, neovascularization and other compensatory mechanisms in chronic endovascular disease have revealed that only a miniscule subset of patients are impacted to any significant extent by slowly progressive obliteration of vessel lumen. We know that even hemodynamically significant endovascular stenosis (specifically defined as >>50% by invasive and interventional cardiologists) is usually well tolerated, as long as there is no acute "plaque rupture" or "thrombosis". Thrombosis and embolism are the end result of a very long and quiescent disease process, but in the absence of such an acute event the body simply forms collaterals and bypasses the obstruction.

D. Rott and D. Leibowitz's "Most Asymptomatic Diabetic Patients Will Not Benefit From Coronary Revascularization", published in the Journal of the American College of Cardiology, Volume 48, Issue 9, Pages 1916-1917, and John G. Webb, MD, Timothy A. Sanborn, MD, Lynn A. Sleeper, ScD, Ronald G. Carere, MD, Christopher E. Buller, MD, James N. Slater, MD, Kenneth W. Baran, MD, Patrick T. Koller, MD, J. David Talley, MD, Mark Porway, MD, and Judith S. Hochman, MD's "Percutaneous Coronary Intervention for Cardiogenic Shock in the SHOCK Trial Registry", published 2001 in the American Heart Journal (141 (6)) are only two of the many clinical trials which have now conclusively proven that attempts to mechanically interfere with this heretofore inexorable process is only useful in the acute setting (i.e.: balloon angioplasty and stenting only work in the setting acute occlusion due to plaque rupture and thrombus, and are not only ineffective, but outright harmful in asymptomatic patients).

The concept of "vaso-occlusive disease" (as opposed to "vaso-occlusive crisis", or "vaso-occlusive event", which, as already discussed, only covers less than 50% of ACS and myocardial infarction patients) is thus outmoded for the above outlined reasons, and has no place in an articulate discussion about an endovascular event. The term is too vague to properly risk stratify a patient and allow determination of an appropriate therapeutic intervention. Further, the body has too many adaptive mechanisms to compensate for chronic (slowly progressive) stenosis for this concept of slow occlusion as a means of functional reduction to have any significance. Unless (as noted below) one proceeds on the assumption that this chronic progressive obstruction is reversible.

The phrase "vaso-occlusive event" (or crisis) should therefore be reserved for the acute setting, but even in that setting has been supplanted by the phrase ACS (Acute Coronary Syndrome), rather than "vaso-occlusive". As used in the prior art, the concept of "vaso-occlusive event" meant rupture of a susceptible plaque with the formation of a locally obstructive thrombus. Such episodes, however, are overt and acute and are detected because of patient symptoms. Patients with vaso-occlusive episodes do not "appear healthy" (if they did, the vessel occlusion would not be diagnosed). The concept of "apparently healthy" patients with "vaso-occlusive" events is nonsensical, since there is no way of identifying such patients. It is not clinically practical to propose attempting to identify patients who appear healthy and yet are having "vaso-occlusive events", in order to determine that they should be subjected to urgent and acute platelet reduction. And, as already mentioned, even if absurd resources were committed to such an undertaking, the Glagov phenomenon tells us that if all early vasculopaths were subjected to invasive angiograms (still the most sensitive technique for detecting vascular stenosis) or equivalent imaging techniques (echocardiogram, vascular ultrasound, CT angiogram or MR angiogram), none of these patients would fall in this early stage into the "vaso-occlusive" category (since their luminal diameter and morphology would be preserved).

CT angiograms are the one exception to this diagnostic quandary. Specifically, CT angiograms can detect changes in the vessel wall, but this qualifies as vascular pathology, not asymptomatic "vaso-occlusive events" or "vaso-occlusive disease". Further, CT angiograms have excellent sensitivity (close to 100%) and thus are excellent for RULING OUT disease, but are not quite so good in terms of specificity (they are not considered an acceptable alternative to fluoroscopic coronary angiography for the purpose of diagnosis and prognosis of endovascular lesions) due to the large number of false positive readings. In fact, many researchers still insist that CT angiograms should only be used for calcium scoring (Agatston calcium score) for risk assessment, rather than evaluation of vessel lumen morophology.

Like angiograms, CT scans can only identify the extent of geometric stenosis, not the risk of an ischemic event that might result from that stenosis.

There is and likely shall remain no way of identifying asymptomatic patients "suffering from vaso-occlusive disease". As mentioned above, asymptomatic patients are triaged for therapy based on exercise tolerance and a risk estimate based on family history and cholesterol levels. These criteria in turn have no correlation to the concept of "vaso-occlusive event", except to assess the downstream risk of such an event occurring within a specified time frame (usually 12 or 24 months). The prospect of a "vaso-occlusive event" has no correlation to the morphologic definition of "vaso-occlusive" as outlined in Hanson's prior art (in other words, there is no such thing as diagnosable "asymptomatic vaso-occlusive disease" that leads to a specific "vaso-occlusive event").

Nevertheless, after all this discussion about the vagueness and contradiction's of Hanson's method(s) (and, specifically, the impracticability of claims 13 and 14 of U.S. Pat. No. 6,585,995, non MPL-pathway inhibitor treatment when " . . . the subject is otherwise free of symptoms calling for treatment with the agent . . . " and " . . . when the subject is apparently healthy . . . "), the most confounding thing regarding these patents is that they are clinically not only not beneficial, but are downright harmful. As confusing as Hanson may be, distilled to its essentials (decrease platelets to treat or ameliorate "vaso-occlusive events"), the method should have demonstrated stellar results. Nevertheless, while there were never any dedicated studies conducted to investigate the merits of Hanson's claims, data extracted from existing studies on anagrelide demonstrated outright harm. "Anagrelide, a therapy for thrombocythemic states: experience in 577 patients." was published in 1992 in the American Journal of Medicine (92:69-78 by the Anagrelide Study Group and reported that: "A clinical trial of anagrelide was conducted in 577 patients with myeloproliferative disorders, including 68 with PV. The open-label trial was conducted over 5 years, with mean treatment duration of 65 weeks. Sixteen percent of the study population discontinued therapy due to adverse events, specifically, headache, diarrhea, edema, palpitations, and abdominal pain. The most common cardiovascular events were palpitations and tachycardia, which occurred in 209 patients (36%). Fourteen patients (2.4%) experienced congestive heart failure, which resolved in most of them with digitalis and diuretic therapy. Cardiovascular adverse events were responsible for discontinuation of therapy by 23 patients (4%). Seven patients died from these events; however, four of them had preexisting coronary artery disease . . . . " " . . . The effect of anagrelide was also studied in another cohort of 942 patients with thrombocythemic states, including 113 with PV. Thirteen percent of patients discontinued the agent due to adverse events such as headache, palpitations, diarrhea, and fluid retention. Palpitations (26%) and fluid retention (22%) were the most common cardiovascular adverse events. There were 50 deaths, including 15 from cardiac causes. [13 . . . . "
" . . . Adverse cardiac effects of anagrelide were assessed in 492 patients with and without significant cardiovascular history. Cardiovascular events, including palpitations, edema, and tachycardia, were generally mild and did not increase cardiovascular disease morbidity. Twenty-two (24%) of 90 patients with history of cardiac disease experienced cardiovascular adverse events, compared with 30 (7%) of 402 patients without such history (p=0.0001) . . . . "

Evidence subsequently emerged that these "mild cardiovascular events" weren't quite so innocuous, especially in the setting of CHF, ACS and myocardial infarction. Christopher W. James, Pharm.D., touched on this topic in his "Anagrelide-Induced Cardiomyopathy: Discussion", published in 2000 in Pharmacotherapy (20 (10)); seven years later this issue was revisited by Lin G M, Chao T Y, Wang W B in their "Acute coronary syndromes and Anagrelide", published in 2007 in the International Journal of Cardiology (117(1):17-9), as well as Doesch C, Krämer B, Geisler T, May, A E, Kroeber S M, Kandolf R, Gawaz, M. in their "Challenges in the treatment of patients with essential thrombocythemia and acute coronary syndrome", published in 2007 in the Journal of Thrombosis and Thrombolysis (August 14).

In fact, the data has been so consistent and disturbing that the FDA mandated the manufacturers of anagrelide to attach a warning to caution against the use of the drug in the setting of CHF, ACS and myocardial infarction. An outcome that is not only counterintuitive, but is nothing short of stunning. Pretty much everybody involved in platelet research had expected that platelets reduction in patients experiencing heart attacks (or "vaso-occlusive crises") would at least prove benign, and had secretly hoped that it might constitute a miraculous cure.

The last thing anybody expected was that less platelets are harmful (aside from increasing the rate of bleeding). Theories naturally abound regarding such a shockingly unexpected finding (refer to Christopher W. James above), but none of the proposed theories are able to explain why platelet-reduction fails to yield aspirin-like benefits. Only the insights and remedies proposed by the current patent are able to overcome these results, which is another reason why the current method qualifies as an invention.

As will be discussed later in the Detailed Description of the Invention, anagrelide's failure to achieve the desired effects has nothing to do with any of the drug's inherent characteristics. Certainly, as all phosphodiesterase inhibitors with generalized effects on cAMP, anagrelide can have significant inotropic effects. However, the negative outcomes noted in the setting of acute cardiac decompensation (under which fall ACS, MI and CHF) are not a consequence of this phosphodiesterase inhibition, but rather a direct result of the bone marrow's response to the reduction of platelets via anagrelide. With appropriate modification of the current methods, or the inclusion of appropriate ancillary modalities in the treatment regimen, the desired treatment goal of reduced cardiovascular events is not only attainable, but assured.

To briefly foreshadow the discussion to follow, it will be explained why pharmacologic means fail in acute vascular occlusion. Adjutant means will be proposed to enhance the methods presented by Hanson. Additionally, the advantage of non-pharmacologic platelet reduction (convenience, cost, predictability, titratability and risk profile) will be discussed. However, the greatest departure from Hanson—and indeed all the prior literature—is the designation of platelets as a causative factor (or, more likely, the primary causative factor) of atherosclerosis itself. The most significant advancement in this application is the promotion of platelets from a dumb, hapless bystander in vascular disease to an important (and probably primary) causative factor of atherosclerosis, endovascular disease and a significant range of other vascular pathologies and related sequelae.

Indeed, this is the first publication to spell out that platelets are much more than a passive component of acute thrombi and emboli, and that perfectly healthy and normally functioning platelets are pathogenic to a healthy and perfectly normally functioning organism in their own right. Which is not an idle piece of trivia, as it is a marvelous coincidence that we do have so many more platelets than we need to safely go about our daily routine, so that we can now safely manipulate these platelet levels with a minimum of complications.

It will also be noted that waiting until an acute crisis occurs is a less than ideal approach. By the time patients have "vaso-occlusive event" or ACS, the patient's entire endovascular interface is profoundly diseased and acute interventions are unlikely to be definitive. Since platelets are only one cofactor in acute vaso-occlusive disease, their manipulation will probably not solve the issue of ischemic crisis. Further, as will be explained in the discussion of anagrelide's dismal failure in "inhibiting and treating vaso-occlusive event", manipulation of platelet concentrations via MPL pathway inhibitors, anagrelide, or any other pharmacologic intervention targeted to the reduction of platelet production is destined to fail. This is in contrast to the overwhelming clinical evidence in favor of chronic manipulation of platelet levels, as in the case of aspirin. Therefore, as with aspirin, intervention should be initiated early (possibly as early as in childhood in patients with known genetic risk), applied widely and with the understanding that it would be most effective in the setting of prevention.

Having exhausted Hanson as a precedent, we next progress to U.S. Pat. No. 7,192,914 (Marth, et al.), which proposes to prevent atherosclerosis through decreasing circulating von Willebrand factor levels (and, specifically, von Willebrand factor multimers). Though they present no bench or clinical data to substantiate their hypothesis, the patent holds it self-evident that von Willebrand factor is directly responsible for the production of atherosclerosis. A subsequent article by Z M Ruggieri entitled "Von Willebrand factor, platelets and endothelial cell interactions", published in 2003 in the Journal of Thrombosis and hemostasis (July; 1(7):1335-42) would appear to confirm these contentions as being prescient: " . . . The adhesive protein von Willebrand factor (VWF) contributes to platelet function by mediating the initiation and progression of thrombus formation at sites of vascular injury. In recent years there has been considerable progress in explaining the biological properties of VWF, including the structural and functional characteristics of specific domains. The mechanism of interaction between the VWF A1 domain and glycoprotein Ib-alpha has been elucidated in detail, bringing us closer to understanding how this adhesive bond can oppose the fluid dynamic effects of rapidly flowing blood contributing to platelet adhesion and activation. Moreover, novel findings have been obtained on the link between regulation of VWF multimer size and microvascular thrombosis. This progress in basic research has provided critical information to define with greater precision the role of VWF in vascular biology and pathology, including its possible involvement in the onset of atherosclerosis and its acute thrombotic complications . . . . "

While this patent, like Hanson, is also a refreshing departure from the current unsubstantiated dogma that cholesterol alone is the primary cause of atherosclerosis, U.S. Pat. No. 7,192,914 (Marth. et al.) fails to recognize that reduction of von Willebrand factor levels translates directly into reduction of platelet activity. What's more, as noted by Miha Furlan, Ph.D., Rodolfo Robles, Miriam Galbusera, Sc.D., Giuseppe Remuzzi, M.D., Paul A. Kyrle, M.D., Brigitte Brenner, Manuela Krause, M.D., Inge Scharrer, M.D., Volker Aumann, M.D., Uwe Mittler, M.D., Max Solenthaler, M.D., and Bernhard Lämmle, M.D. in their "Von Willebrand Factor-Cleaving Protease in Thrombotic Thrombocytopenic Purpura and the Hemolytic-Uremic Syndrome.", published Nov. 26, 1998 in The New England Journal of Medicine, Volume 339:1578-1584, Number 22, under some circumstances, disturbances in von Willebrand factor metabolism even translate directly into thrombocytopenia.

Thus, even if the reduction in atherosclerosis suggested in the setting of von Willebrand's disease from pig studies (refer to the previously referenced article by Valentin Fuster and E. J. Walter Bowie, "von Willebrand's disease in pigs and atherosclerosis", published October 1979 in the International Journal of Clinical & Laboratory Research, Volume 9, Number 4) were to be confirmed in human cohorts, platelet reduction would be far more likely to be responsible for the lowered incidence of atherosclerosis than the decrease in the von Willebrand factor itself. Lowering platelet levels directly is therefore likely to result in a much greater impact than addressing von Willebrand factor levels. Additional reduction of von Willebrand levels in the face of the currently proposed direct platelet therapy may provide additional therapeutic efficacy in terms of inhibition of atherosclerosis and vascular disease, but that is not the intent of Marth et al. In terms of reduction of von Willebrand factor having any relevance to the current application, Marth et al. must be rejected in view of the fact that there is no mention of reduction of platelet counts, platelet volumes or platelet activity.

Puzzlingly, Burnett et al., USPTO publication number 20080070890, was also cited in the examination of prior U.S. patent application Ser. No. 11/868,393 (which constitutes the basis for this Continuation in Parts), though it has no relationship whatsoever to neither the original, nor the current application. It talks about the use of Spirocyclic Azetidinone Compounds, compositions comprising a Spirocyclic Azetidinone Compound and methods for treating or preventing a disorder of lipid metabolism, pain, diabetes, a vascular condition, demyelination or nonalcoholic fatty liver disease, comprising administering to a patient an effective amount of a Spirocyclic Azetidinone Compound. There appears to be no connection between this item and the current application (or the one upon which it is based), so it will not be discussed any further.

Similarly, Aslanian et al USPTO publication 20080076750, "Azetidinone Derivatives and Methods of Use Thereof" (" . . . methods for treating or preventing a disorder of lipid metabolism, pain, diabetes, a vascular condition, demyelination or nonalcoholic fatty liver disease, comprising administering a compound having the formula or a pharmaceutically acceptable salt, solvate, ester, prodrug or stereoisomer thereof, wherein: R.sup.1 and R.sup.2 are defined in Tables 1-6 herein, and R.sub.3 is -phenyl, -4-chlorophenyl, -2-pyridyl, or -3-pyridyl.) and USPTO publication 20080076751, "Azetidinone Derivatives and Methods of Use Thereof" (" . . . Azetidinone Derivatives, compositions comprising an Azetidinone Derivative and methods for treating or preventing a disorder of lipid metabolism, pain, diabetes, a vascular condition, demyelination or nonalcoholic fatty liver disease, comprising administering to a patient an effective amount of an Azetidinone Derivative.") were also cited as part of the above mentioned examination, but bear no relevance either to the original, or the current application. Thus, these items are also not deserving of any further mention.

In addition to the lack of relevant prior art, it will also be demonstrated that the improvements proposed herein are by no means obvious and are based on the fundamental insight that platelets are not merely a component of obstructive thrombi due to atherosclerosis, but are themselves either a contributive or outright causative factor (even at normal counts) of. very wide range of cardiac, microvascular and macrovascular pathologies.

BRIEF SUMMARY OF THE INVENTION

A vast body of evidence exists to prove that the preponderance of vascular disease and sequelae popularly attributed to cholesterol in fact has little to do with it. Cholesterol is and remains nothing more than a weak risk factor in the development of atherosclerosis and in pathogenetic terms is no more than a necessary cofactor. The majority of vascular disease and its sequelae are due to excess total circulating platelet activity. This is to be expected, as total circulating platelet activity was calibrated through millions of years for survival in a primitive environment and is unnecessarily high for many species in a protected setting, humans among them.

Fortunately, clinical data suggests even drastic reduction of this platelet activity does not result in any excess bleeding for most otherwise healthy individuals. Such reduction in platelet activity, in turn, results in elimination of the vascular disease and its sequelae due to this unnecessarily high total plasma platelet activity.

Reduction of total circulating platelet activity via use of aspirin has already been demonstrated to be highly effective in prevention and treatment of vascular disease and its sequelae. For further gains and conceivably even complete elimination of many different types of vascular disease and its sequelae, however, more categorical measures need to be taken to curtail total body platelet activity even further.

Reduction of total circulating platelet activity may be accomplished via pharmacologic or non-pharmacologic means, but must include reduction in actual number of circulating platelets. Any proposed therapy may not allow even a brief transient intermediary state of elevated total circulating platelet activity, such as happens with the use of platelet reducing drugs and, indeed, any modality in the acute phase as a result of the bone marrow's attempt to compensate for any insult targeting platelets.

Particular care must be taken to avoid this temporary rise in hemostasis for acute coronary syndromes and myocardial infarction. For this reason mechanical means are preferred in the acute phase of obstructive, thrombotic or embolic disease.

Extravascular sequelae of vascular disease, most of which at present are not recognized as such, are also to be included in this treatment strategy.

Various indices are discussed to guide and monitor therapy.

DETAILED DESCRIPTION OF THE INVENTION

Hippocrates, the originator of modern medicine, suggested any proposed therapy must satisfy three essential criteria: 1) it must do no harm, 2) it must be appropriate to the pathology and 3) it must have measurable effects. Unfortunately, however, a fourth principle dominates today's highly technological and financialized medical market: it must be cost efficient—i.e. make a profit for the right parties.

A significant majority of modern medical interventions have been demonstrated satisfy only the fourth criterion, yet they persist in the medical marketplace. Vascular surgery, for instance, is categorically harmful by Hippocrates' most basic of principles: in excess of 20% of vascular surgery subjects die within the peri-operative time period. Drugs like Actos and Avandia, which are lethal, persist in the marketplace. So do Vioxx and Celebrex. Cholesterol reducing drugs have questionable efficacy at best, and Aricept, the king of the "emperor has no clothes" drugs is absolutely useless.

However, it is the second criterion, namely being appropriate to the pathology, that trips up most medical therapies. Most medical treatments through history have been applied without the slightest understanding of the mechanism of their effect, which makes it quite impossible to prove whether they are in fact appropriate to the entity being treated. Even highly effective modalities can thus be considered to be suspect, since many patients shall be treated who really shouldn't, while many who would benefit from the treatment will not receive it.

One old time remedy that falls into this category is bloodletting. Phlebotomy was practiced essentially indiscriminately through the "dark ages", though there were some criteria for its use: " . . . But blood is let by opening a vein for five respects: the first to lessen the abundance of blood, as in plethoric bodies, and those troubled with plentitude. The second is for diversion, or revulsion; as when a vein of the right arm is opened to stay the bleeding of the left nostril. The third is to allure or draw down, as when the vein is opened in the ankle to draw down the menstrual flow in women. The fourth is for alteration or introduction of another quality, as when in sharp fevers we open a vein to breathe out that blood which is heated in vessels, and cooling the residue which remains behind. The fifth is to prevent imminent disease, as in the spring and autumn we draw blood by opening a vein in such as are subject to spitting of blood, quinsy, pleurisy, falling sickness, apoplexy, madness, gout, or in such as are wounded, for to prevent the inflammation which is to be feared. Before bloodletting, if there be any excrement in the guts, they shall be evacuated by a gentle clyster, or suppository, lest the mesenteric veins should thence draw unto them any impurity . . . . "

Bloodletting is ridiculed today as a completely pointless enterprise. Yet, although paraded as an example of "outdated superstitions", bloodletting very probably saved many lives if applied in the setting of myocardial ischemia, as well as some other thrombotic states. As is the case with most treatments, the key factor determining the efficacy of bloodletting is patient selection. Gout, for example, qualifies as an excellent potential disease to be treated. So does polycythemia vera (in fact, bloodletting—now politely termed "phlebotomy"—is one of the treatment modalities of PV). Anemia? Clearly a no-no. Most other diseases listed in the above paragraph fall somewhere between those extremes.

As with phlebotomy, all treatments need clear criteria for their use. Our sophisticated medical industry pretends to infallibility, but none of our modern interventions are without risk. In fact, given the increased intrusiveness of modern medicine, Hipocrates' caution to "first do no harm" is more relevant than ever. Particularly when it comes to manipulating arguably the second most important component our body (hopefully, for most people, after their brain).

Treatments must be safe in general, not just when compared to the worst alternative. This is not the case with the prior art to this patent. Though there is ample evidence to show that platelets are the central cause of endovascular luminal disease, as well as a vast host of pathologies related to the same, and thus a gut level expectation would be that any reduction of these platelets would save lives in the event of heart attacks, the evidence is incontrovertible that tampering with platelets in a careless manner (i.e.: as recommended by Hanson) leads to poor outcomes.

The Hanson patents are a perfect illustration of an apparently logical and well-intentioned therapeutic approach gone bad. As demonstrated in the prior discussion, Hanson's "vaso-occlusive events" reduce in clinical practice to ACS and heart attack; treating ACS and heart attacks by reducing platelet counts via a drug that can be equated to aspirin in its side effect profile (as claimed by the company selling the drug) was a neat proposal that must have sent chills down the spines of intensivists and cardiologists. Reduction of platelet counts in the acute phase of ischemia stood a real chance of revolutionizing cardiology. So what "went wrong"?

Aside from the aforementioned carelessness both on the part of the patentee and examiner for U.S. Pat. Nos. 6,585,995 and 7,022,521? Nothing. As early as 1989 M. Packer noted in his "Effect of phosphodiesterase inhibitors on survival of patient with chronic congestive heart failure", published in the American Journal of Cardiology (63:41A-5) the negative effects of anagrelide in CHF; together with the results of the aforementioned Anagrelide Study Group, published in 1992 (close to a decade prior to the application for U.S. Pat. No. 6,585,995), this data should have been known to a specialist in the study of platelets and platelet-related disease.

Short of calling the inventor and patent examiner disingenuous, one can only ascribe such a gross error to carelessness. Which does not change the fact that when this particular patent issued, it was already known that it was dangerous and harmful to treat ACS with anagrelide. As for the manufacturer, there were continued attempts to find a justification for use of their drug in acute coronary disease in spite of the existing evidence. In fact, it would be 2005 before the manufacturer would be finally forced into the following caution (see http://www.merck.com/mmpe/lexicomp/anagrelide-.html): " . . . Disease Related Concerns: Cardiovascular disease: Use with caution in patients with known or suspected heart disease; tachycardia, orthostatic hypotension, and heart failure have been reported. Pretreatment cardiovascular evaluation and careful monitoring during treatment is recommended . . . . " " . . . Adverse reactions: Cardiovascular: Peripheral edema (9%), chest pain (8%), tachycardia (8%), angina, arrhythmia, cardiovascular disease, CHF, hypertension, postural hypotension, syncope, thrombosis, vasodilatation . . . " " . . . Frequency not defined: Atrial fibrillation, cardiomegaly, cardiomyopathy, cerebrovascular accident, complete heart block, deep vein thrombosis . . . . "

Without invoking an outright conspiracy, one must also regard with some degree of suspicion why the failure of a single drug (i.e.: anagrelide) led to the abandonment of an entire methodology (i.e.: platelet reduction to prevent and treat ACS). As noted in the Prior Art, instead of the "simplest explanation" (Numquam ponenda est pluralitas sine necessitate—"Plurality must never be posited without necessity"; the principle popularly known as Occam's Razor states that the simplest explanation is usually the correct one) there are some seriously convoluted rumors circulating regarding the mechanism whereby anagrelide is supposed to lead to bad outcomes in CHF.

Packer and James (see above) insist that anagrelide harmful effects originate from its inotropic effects. Christopher W. James expounds this "fact" authoritatively, though there isn't a single shred of evidence to support the contention that the phosphodiesterase effects of anagrelide are what's responsible.

Instead, not a single "authority" has remarked on what is known fact: anagrelide does bad things to platelets. Returning once more to laboratory science, the proposed mechanism of action for anagrelide provides a clue to the causes of this paradoxical clinical outcome: " . . . Anagrelide appears to inhibit cyclic nucleotide phosphodiesterase and the release of arachidonic acid from phospholipase, possibly by inhibiting phospholipase $A_2$. It also causes a dose-related reduction in platelet production, which results from decreased megakaryocyte hypermaturation (disrupts the postmitotic phase of maturation) . . . . "

The above quote is from Bailliere's Clinical Haematology, Megakaryocytes and Platelet disorders, published February 1997 (the year after anagrelide's US market debut). The authors, Bernd van der Loo, MD and John F. Martin, MD noted anagrelide not only lowers platelet counts, but alters platelet morphology. The next year Bellucci, S., Legrand, C., Boval, B., Drouet, L. and Caen, J. detailed anagrelide's contortive effect on megakariocytes in their "Studies of platelet volume, chemistry and function in patients with essential thrombocythaemia, published in the British Journal of Haematology: "Anagrelide (imidazoquinazolin derivative) is a new compound proposed for the treatment of myeloproliferative disorders . . . . " " . . . The aim of this study was to test the effect of this drug not only on the platelet count but also on platelet volume, chemistry and function, which has not previously been reported. Thus, in ET, different functional or structural platelet abnormalities were reported: a shortening of the bleeding time, hypoaggregation to several agonists, and in particular a lack of response to adrenalin, an increase in the amount of total platelet glycoprotein IV (or CD36), and an abnormal migration of thrombospondin on electrophoresis. These different parameters were studied before and during therapy with Anagrelide. Although the platelet count was corrected, no functional or chemical abnormality was improved. Furthermore, platelet volume was shown to be constantly increased under Anagrelide. Thus, Anagrelide, in reducing the platelet count, may possibly decrease the risk of thrombosis and haemorrhage. Nevertheless, if the risk of thromboses and/or myelofibrosis is related not only to the platelet count but also to the platelet abnormalities, the persistence of a thrombocytopathy in patients treated with Anagrelide must be taken in consideration . . . . "

Claire N. Harrison, M.R.C.P., M.R.C.Path., Peter J. Campbell, F.R.A.C.P., F.R.C.P.A., Georgina Buck, M.Sc., Keith Wheatley, D.Phil., Clare L. East, B.Sc., David Bareford, M.D., F.R.C.P., Bridget S. Wilkins, M.D., F.R.C.Path., Jon D. van der Walt, M.D., F.R.C.Path., John T. Reilly, F.R.C.P., F.R.C.Path., Andrew P. Grigg, F.R.A.C.P., F.R.C.P.A., Paul Revell, M.D., F.R.C.P., Barrie E. Woodcock, F.R.C.P., F.R.C.Path., Anthony R. Green, F.R.C.Path., F.Med.Sci. correlated these findings with clinical outcomes in their "Hydroxyurea Compared with Anagrelide in High-Risk Essential Thrombocythemia/Primary Thrombocythemia 1 Study, for the United Kingdom Medical Research Council", published Jul. 7, 2005 in the New England Journal of Medicine (Volume 353:33-45). The authors concluded that: " . . . Though "After a median follow-up of 39 months, patients in the anagrelide group were significantly more likely than those in the hydroxyurea group to have reached the primary end point[1] (odds ratio, 1.57; 95 percent confidence interval, 1.04 to 2.37; P=0.03) . . . ", nevertheless " . . . As compared with hydroxyurea plus aspirin, anagrelide plus aspirin was associated with increased rates of arterial thrombosis (P=0.004), serious hemorrhage (P=0.008), and transformation to myelofibrosis (P=0.01) but with a decreased rate of venous thromboembolism (P=0.006). Patients receiving anagrelide were more likely to withdraw from their assigned treatment (P<0.001). Equivalent long-term control of the platelet count was achieved in both groups . . . . "

Interestingly, instead of calling for more research to find modalities to ameliorate anagrelide's effect on platelets, the group concluded that: " . . . Hydroxyurea plus low-dose aspirin is superior to anagrelide plus low-dose aspirin for patients with essential thrombocythemia at high risk for vascular events . . . ." While they agreed that anagrelide performs its primary therapeutic role of platelet reduction with admirable efficacy, they felt that anagrelide should remain a second-line drug in such patients because due to its complex cardiovascular effects.

However, closer scrutiny of these effects (i.e.: increased platelet volumes, more precursors and immature platelets and more bizarrely formed platelets) will reveal that some of these complications aren't particular to anagrelide, but are based on the bone marrow's response to any insult that lowers any blood cells. The bone marrow responds to such stimuli by ramping up production and dumping precursors into the peripheral circulation. What's more, even some (or many) of the cells that appear to have proceeded fully through the differentiation process are not fully mature. Their function is thus suspect; in the case of platelets, the fine balance between their tendency to spontaneously activate and not be able to activate at all is in jeopardy.

Increased mortality in the setting of "vaso-occlusive events" is thus due to the bone marrow's response in the face of effective platelet reduction with anagrelide. While the above study conclusively demonstrates that there is some excess risk with anagrelide as compared to alternative therapies, this purported "anagrelide effect" is not an "anagrelide effect" at all and will be seen with any interventions which reduce platelet counts acutely.

In fact, at least three studies suggest that vascular mortality in the acute phase of all heart attacks is at least in part due to changes to platelet morphology that have nothing to do with anagrelide and occur spontaneously in the acute phase of vascular occlusion. L. Pizzulli, A. Yang, J. F. Martin and B. Lüderitz note in their "Changes in platelet size and count in unstable angina compared to stable angina or non-cardiac chest pain" published in 1998 in the European Heart Journal (19 (1): 80-84), N. Lakkis, H. Dokainish, M. Abuzahra, V. Tsyboulev, J. Jorgensen, A. Ponce De Leon, and A. Saleem in their "Reticulated platelets in acute coronary syndrome: A marker of platelet activity.", published 2004 in the Journal of the American College of Cardiology (44(10): 2091-2093) and Giuseppe Lippi, Luca Filippozzi, Gian Luca Salvagno, Martina Montagnana, Massimo Franchini, Gian Cesare Guidi, Giovanni Targher in their "Increased Mean Platelet Volume in Patients With Acute Coronary Syndromes., published 2009 in the Archives of Pathology & Laboratory Medicine (Vol. 133, No. 9, pp. 1441-1443) all note that platelet morphology is altered in ACS in a manner consistent with the presence of a higher percentage of irritable or activated platelets.

M P Ranjith, R Divyal, V K Mehtal, M G Krishnan, R KamalRaj, Arvind Kavishwar are even more explicit in their "Significance of platelet volume indices and platelet count in ischaemic heart disease", published 2009 in the Journal of Clinical Pathology (62:830-833) are even more explicit in this respect. The authors noted that the platelet count was significantly lower(!!) in patients with acute coronary syndrome ($201.28 \times 10^9$/l) as compared with patients with stable angina ($267.07 \times 10^9$/l) and those from the normal population ($256.65 \times 10^9$/l) (p<0.001). In addition, patients with acute coronary syndrome had higher platelet volume indices (10.97) compared with patients in the stable angina (10.03) and normal population groups (9.12) (p<0.001). They concluded that because patients with acute coronary syndrome had higher platelet volume indices and lower platelet counts compared with those with stable angina and the normal population, measurements of platelet volume indices and platelet count may be of some benefit in detecting those patients at higher risk for acute coronary events. For some puzzling reason, however, they failed to make the creative leap to suggest actively reducing platelet volumes to treat ACS At the risk of belaboring this point, similar changes occur spontaneously in the acute phase of all vascular occlusion. Presuming the body has some protective mechanisms to reduce platelet counts in the case of acute platelet-related pathology, these mechanisms appear to be sabotaged by the bone marrow's inability to "let go". For this reason, unless additional measures are taken to regulate the clotting and coagulation mechanisms (or unless activated platelets are somehow mechanically separated from the blood), acute platelet reduction will prove lethal.

The current patent is thus the first to present the surprising insight that platelet count reductions in the acute setting are going to be ineffective unless the applied method is non-traumatic and non-activating in regards to existing platelets, as well as the new platelets to be released by megakaryocytes. The current application also emphasizes that pharmacologic means of reduction are not likely to be effective in the acute phase for this same reason. Specifically, since all platelet production inhibitors would have to affect megakaryocytes, they are all going to likely disregulate the function of the produced platelets. Since the platelet/coagulation system is very tenuously balanced, any random disturbance is likely to result in a negative outcome—particularly in the transitory phase to a new equilibrium, where platelet activity by definition is in a state of flux.

One issue that is solely a function of pharmacologic modes of platelet reduction, however, is the delay in the onset of action. While platelets do have a short lifespan, even total shutdown of the bone marrow will require at least a week before platelet levels decrease significantly. For this reason (as well as the previously described increase of premature platelets and precursors), platelet reduction solely by pharmacologic means (or, more specifically, platelet reduction by pharmacologic inhibition of platelet production and/or release into the bloodstream) is unfortunately of no use in clinical practice in the setting of acute "vaso-occlusive events".

The claims of the prior art do not include non-pharmacologic intervention as a means of platelet reduction in the setting of acute vaso-occlusive events (Hanson's claims are very explicit in prescribing pharmacologic intervention only to inhibit megakaryocyte production of platelets), contributing to the lack of clinical efficacy (or, rather, to the negative clinical efficacy) of the proposed methods. And pharmacologic platelet reduction also carries another significant downside: the risk of excessive platelet depletion. Pharmacologic inhibition of platelet inhibition means that no reserve platelets will be available in the case of an overshoot (or, more correctly in this case, an undershoot). Additionally, fine control is not possible given the drastic bone marrow suppression required in the acute care setting.

Extracorporeal (non-pharmacologic) platelet reduction techniques such as plateletpheresis address these deficiencies. Plateletpheresis (or analogous, but improved mechanical means) easily achieves a sufficiently rapid and intense drop in platelet levels to make a clinically relevant impact. Additionally, fine control of platelet levels is possible and platelets can be banked to deal with the previously mentioned overshoot (undershoot). Not to mention, a very important side benefit of non-pharmacologic methods is that left over platelets can be used to transfuse chemotherapy and trauma patients, a benefit for society at large, as platelets are in chronic shortage.

As mentioned before, however, even non-pharmacologic modalities will require modulation of platelet activity and coagulation to prevent an undesirable shift in the activity profile of these mechanisms. Such measures may include, but are not restricted to, modification of platelet separation processes that would preferentially preserve only a platelets that fall within a specified range of volumes, as well as techniques to filter plasma, or otherwise extract any substances produced during the plateletpheresis process. The current patent recommends the use of specific indices to ensure that individual platelet activity profile remains the same after treatment. Assessment of platelet activity might include direct platelet function assay (PFA) and bleeding time, or surrogate assays such as platelet volume and PDW.

When possible, it is recommended that functional assays be utilized to estimate total platelet activity directly. However, an easy and inexpensive surrogate index for this total body platelet activity in the setting of chronic therapy (i.e.: during steady state, when the bone marrow equilibrates to the point where average platelet volumes and platelet morphology can be assumed to be constant) might be total body platelet volume, with additional information provided by the aforementioned PDW, or Platelet Distribution Width. PDW (Platelet Distribution Width) is a little used index analogous to RDW (Red Cell Distribution Width; as early as 1997 Jean-Claude Osselaer, Jacques Jamart and Jean-Marie Scheiff remarked on the possible uses of this index in their "Platelet distribution width for differential diagnosis of thrombocytosis" (published in Clinical Chemistry, 43:1072-1076).

At times (as in during the aforementioned steady state) even platelet counts may suffice as an index of therapy. Which brings us back to the issue of chronic versus acute intervention. Not only is it more problematic to try to titrate and monitor treatment in the acute phase via pharmacologic means, but the current patent emphasizes preventive treatment for another reason as well: an "acute vaso-occlusive event" is analogous to an "overnight success". Destruction of vessel walls is a decades' long labor of love (read: Western Diet); the damage does not happen overnight, nor does it cease instantly after treatment. ACS in its full scope is but a minute segment of the endovascular disease continuum and this patent thus emphasizes the need for ongoing treatment, as well as ongoing accurate monitoring of treatment effects.

Paradoxically, the currently proposed advancements may resurrect the concept of vaso-occlusive disease. In the past, poor clinical outcomes of treatments based on this initially promising concept have frustrated clinicans and researchers alike. However, the ability to reverse even advanced disease would once again make useful the detection of luminal irregularities as a marker of endovascular disease. The removal of excessive platelets and chemicals released during their activation might make it possible to prevent true "vaso-occlusive events" (the whole constellation of ACS, not the narrow subset defined by Hanson, but as occurs in real life) and even reverse disease that at present the body can only compensate for by indirect means.

But whatever the final terminology will emerge for Acute Coronary Syndrome, one must keep in mind that, unlike endovascular disease on a chronic basis, platelets are only be one of many cofactors in the genesis of acute "vaso-occlusive events". Thus, their manipulation is not likely to completely solve the issue of ischemic crisis. Also, the damaged vessel(s) will remain after the event. For this reason, a vague recommendation such as "reduction of platelet counts to "at least low normal" is unlikely result in a significant long term clinical effect.

Conversely, Hanson's hodgepodge approach and focus on the heroic and visually dramatic concept of reduction of occlusion and thrombosis clearly demonstrates ignorance regarding the pathogenetic nature of even low normal platelet counts in otherwise perfectly healthy individuals. It also misses the only viable use of pharmacologic methods in the treatment of vascular disease: chronic therapy and prevention.

It should be clear from the prior discussion that chronic attenuation of total circulating platelet activity will arrest and even reverse endovascular disease. The role of pharmacologic modalities is hard to predict, even when accompanied by appropriate adjunct methods to prevent fluctuations in this index, as well as coagulation; most likely the primary benefit of such methods over the more precise mechanical reduction will be cost. However, it must be emphasized that pharmacologic means of platelet reduction will always carry some inherent risk in terms of platelet morphology variability, which translates directly into an increased risk of spontaneous coagulation and thrombus formation, as compared to the mechanical alternatives.

Hanson again appears oblivious to this issue of treatment risk when he recommends blindly treating all patients with "vaso-occlusive events", including those who are asymptomatic, or even "appear healthy". Patients with such occult disease subjected to even a slight temporary increase in total body platelet activity (which, as discussed above, is an inevitable intermediary state in the initial stages of pharmacologic platelet reduction) will have a statistically increased rate of ACS and myocardial infarction.

Since even perfectly compliant patients will experience such fluctuations with pharmacologic treatment, there will be times when in fact the treatment may directly contribute to endovascular events. The situation would become far more dramatic in the all too common non-compliant patient who only takes their medicine sporadically. Such patients would experience drastic (and tragic) fluctuations on their total circulating platelet activity, resulting in periodic clonidine-like rebounds in their pathology during the times when they are non-compliant (clonidine, an anti-hypertensive, is notorious for causing "rebound hypertension" if the drug is stopped abruptly, which is why it must be tapered slowly).

For this reason, unlike Hanson, the current application focuses on decreasing platelet activity, not platelet counts (refer to the section on von Willebrand factor regarding the discussion noting the lack of congruity of these two terms), as the ultimate aim of treatment. Also unlike Hanson, the current application prescribes chronic modulation of platelet activity, whether initiated by an acute event, or not, or whether achieved quickly or not. As with aspirin, it is recommended that intervention should be initiated early (possibly as early as in childhood in patients with known genetic risk), applied widely and with the understanding that it would be most effective in the setting of prevention. And, finally, also unlike Hanson, this application does not permit transient increase of platelet activity. In other words, though platelet counts may decrease satisfactorily, any platelet activity assays must also ascertain the level of activation and irritability of individual platelets, as averaged over the whole available platelet population, have also decreased.

Which doesn't necessarily mean that the method proposed by this application must inevitably place one more onerous burden on our already overly extended healthcare industry (i.e: in terms of testing costs). We known that there is little, if any increase in hemorrhage until platelet counts drop below 50 k per cubic microliter, as long as the platelets present are normal. Considering the population average of 200 k to 250 k, one can assume that up to 80% reduction in total body platelet activity is likely to be tolerated without any ill effects.

Considering the decades required to develop most types of vascular disease and the minute imbalances that are probably responsible, as well as the fact that platelets elaborate and release at least some humoral with a significant role in the genesis and progression of vascular injury that have zeroth order kinetics (zeroth order kinetics, also called saturation kinetics, means that the substance is cleared at a steady rate regardless of its concentration), it is likely that even a 50% reduction in total circulating platelet activity will have a dramatic therapeutic impact (as has already been proven with aspirin, a far less aggressive therapy than proposed by this patent). This leaves a huge therapeutic margin, which means that, unlike with coumadin therapy, testing would be infrequent and with an eye on guiding therapy, rather than stringent and with a desperate mandate to keep patients on the razor edge of maximum therapeutic efficacy.

Since acceptable rates of major bleeding depend on the nature of the projected or already existent pathology (to compare with coumadin once more, target INR values for coumadin therapy are different for prosthetic mitral valve implants as compared to atrial fibrillation, for instance), testing regimens can thus be individually tailored. Reduction in platelet counts can be combined with selective platelet inhibition to reduce the activity of the platelets that do remain, as well as to block the effect of substances secreted by the platelets. As mentioned, platelet function and coagulation assays can be used as an adjunct to further refine the precision of platelet function manipulation.

Generally, platelet counts are envisioned to be reduced to between 50000 to 150000 per microliter (as mentioned above, platelet counts are only a quick and dirty method for monitoring therapeutic effect once platelet activity has stabilized and would only serve in the steady state), based on the nature of the pathology to be avoided or treated. Advanced atherosclerotic disease, coronary or peripheral vascular, will require more aggressive reductions. Early and advanced CNS microvascular/microfibrillary disease would similarly mandate very aggressive management. Patients with artificial cardiac valve implants such as bileaflet (St. Jude's) mechanical valves, particularly in the mitral location, would also require particularly aggressive management (i.e.: low target platelet levels).

Haemodialysis patients should be treated through combined pharmacologic and mechanical separation means. It is envisioned that the long term future of haemodialysis shall be in the more physiologic, longer and less intensive forms, such as ultrafiltration and SLED (sustained low efficiency dialysis). While these might be less irritating to platelets, and therefore more benign to the endothelium, it is nevertheless prudent to minimize the number of platelets transiting through the haemodialysis circuitry. It is thus proposed that all forms of mechanical haemodialysis shall require an extracorporeal separation stage with or without chronic platelet inhibition and chronic platelet level reduction as part of the haemodialysis process.

Finally, to address this patent's insistence on including "the sequelae of vascular disease" into the umbrella of treatable conditions, there are multiple conditions with extensive literature documenting a link to platelet activity. Malignancy in specific does have a well documented vascular component in its genesis and reduction of total circulating platelet activity is a novel means of slowing and possibly even arresting the progress of some highly vascular cancers (or cancers demonstrated to depend on vascular growth factors). Similarly, hemodialysis and other renal replacement therapy provides a perfect setting for implementation of this technology due to the known activation of platelets during hemodialysis and hyperfiltration (refer to Thijs A, Grooteman M P, Zweegman S, Nubé M J, Huijgens P C, Stehouwer C D, "Platelet activation during haemodialysis: comparison of cuprammonium rayon and polysulfone membranes", published 2007 in Blood Purification, 25 (5-6):389-94), and the horrendous vascular pathology that arises from said activation (Kristian Kunz, Philippe Petitjean, Mohamed Lisri, Frances Chantrel, Christian Koehl, Marie-Louise Wiesel, Jean-Pierre Cazenav, Bruno Moulin and Thierry P. Hannedouche, "Cardiovascular morbidity and endothelial dysfunction in chronic haemodialysis patients: is homocyst(e)ine the missing link?", published 1999 in Nephrology Dialysis Transplant, 14: 1934-1942).

DESCRIPTION OF SPECIFIC EMBODIMENTS

Several mechanical methods are currently available to reduce platelet counts in human beings. The most obvious and widely used is plateletpheresis, a centrifugal elimination of platelets from the blood. Relatively atraumatic, it does result in activation of some platelets.

Filters and adsorbent substrates are also used to eliminate platelets from blood. These would be considered inadvisable given the amount of platelet activation prior to sequestration from the blood stream.

Long term ideal separation of platelets from blood would probably require complete blood decomposition and removal of platelets from serum as the last component. This sort of mechanical separation and reconstitution would serve as the mainstay for patients who already have advanced vascular disease and who also have thrombocytopenia (such as hemodialysis patients).

Anagrelide is a substance known to inhibit the production of platelets. Currently it is only used to reduce counts in patients with thrombocytosis (or high platelet counts). Unfortunately, anagrelide has been implicated in precipitating acute coronary syndromes, including heart attacks. On the face this might therefore be considered a second line agent. However clinical experience of use of Anagrelide concerns only patients with ELEVATED platelet counts—who are already at excess cardiovascular risk. It might be found that anagrelide presents acceptable risks when reducing platelet counts from normal levels.

The only viable alternative to anagrelide available at present (hydroxyurea) is too toxic for any but the sickest patients.

The administration of anagrelide is known to reduce platelet counts with significant impact on the morphology and activity of the platelets produced by megakaryocytes influenced by it. This means that reduction below population norms (specifically 150000 platelets per cubic microliter of blood) may contribute to increased intravascular events, even at platelet counts significantly below low population norms (specifically 150000 platelets per cubic microliter of blood). However, such a finding would easily be remedied by the use of aspirin, clopidogrel or a similar antiplatelet agent.

Similar, but more effective and/or less harmful medicines such as monoclonal agents or more specific bone marrow modulators, might emerge once the market realizes the therapeutic potential. Targeted monoclonal total circulating platelet activity is potentially very effective and presents few side effects, as demonstrated by patients with HIT (heparin-induced thrombocytopenia), who are remarkably free of bleeding and other side effects in spite of precipitously reduced platelet counts (around 8 k to 10 k per cubic microliter). This patent is to include the use of such monoclonal (or polyclonal auto-immune) pharmacologic platelet reduction for the purpose of addressing vascular disease and its sequelae as outlined in other parts of this patent application.

Further possibilities of platelet reduction might include whole blood removal (phlebotomy), selective malnutrition, or monoclonally or passively activated platelet removal via adherence or macroclumping and filtration and then subsequent plasma treatment if necessary. Any process proven of low morbidity and high efficacy in this regard would be viable. The addition of a platelet pheresis stage to a perfusion circuit, extra corporeal membrane oxygenator and hemodialysis circuit is an application that requires a mechanical application. This mechanical separator would have to be more temporally efficient then current plateletpheresis equipment, possibly necessitating the addition of a passive or active platelet activating sequence and subsequent cluster filtration and plasma treatment independent of the perfusion circuit, extra corporeal membrane oxygenator or hemodialysis circuit.

A novel platelet separator (U.S. Pat. No. 7,655,124) utilizing electric fields and/or mixed phase reactions is referenced as a possible device to realize the desired platelet counts and total circulating platelet activity. It is hoped that this technology will enable a traumatic separation of platelets from blood with sufficient efficiency to both prevent platelet-related morbidity and to permit use in real time applications.

Although the foregoing invention has been described in some detail by way of illustration and example for purposes of clarity of understanding, it will be understood that certain changes and modifications may be practiced within the scope of the appended claims. Thus, in accordance with the foregoing disclosure, the invention is not to be limited by the examples and descriptions herein, but is to be determined in scope by the claims provided.

What is claimed is:

1. A method for reducing the incidence and severity of vascular disease and its sequelae, comprising the steps of:
   1) identifying candidates at risk selected from the group consisting of: reduced mobility, smoking, oral anti-contraceptive, hormone replacement therapy or testosterone use, elevated platelet counts, obesity, diabetes, elevated cholesterol, elevated lipids, atherosclerosis, peripheral vascular disease, arterial thrombosis, stent thrombosis, coronary graft thrombosis, peripheral bypass graft thrombosis, venous thrombosis, microvascular thrombosis, heart valve thrombosis, arterial emboli, venous emboli, microvascular emboli, arterial stenosis, myocardial infarction, infarction of other organs, transient ischemic attack, stroke, arrhythmias, congenital cardiac malformations, radiotherapy to the chest, age above a certain pre-determined threshold, genetic or acquired coagulopathies, hemodialysis, or family history of any of the above;
   2) reducing the total circulating platelet activity below normal levels without a transient increase in the total circulating platelet activity, or a transient or permanent increase in the total number of platelets, activated platelets, immature platelets or platelet precursor cells in the peripheral circulation;
   3) surveillance of the patient for occult or overt bleeding, or other undesirable effects of treatment;
   4) periodic re-evaluation of the patient's risk factors.

2. The method of claim 1 wherein the method utilized to reduce the total circulating platelet activity is pharmacologic.

3. The method of claim 1 wherein the method utilized to reduce the total circulating platelet activity is non-pharmacologic.

4. The method of claim 1 wherein the method utilized to reduce the total circulating platelet activity includes any combination of pharmacologic, mechanical, electric, electronic, or electromechanical means.

5. The method of claim 1 wherein the reference normal is the patient's own levels, measured acutely or averaged over time.

6. The method of claim 1 wherein the reference normal is the normal range for the general population.

7. The method of claim 1 wherein the reference normal is the lower limit of normal for the general population.

8. The method of claim 1 wherein said method further, includes a reduction in the average individual platelet volume.

9. The method of claim 8 wherein said reduction in the average platelet volume is achieved through, the selective reduction of the number of platelets with larger volumes.

10. The method of claim 8 wherein said method the reduction of platelet volume to the final target levels is achieved gradually.

11. The method of claim 1 wherein said method further includes the administration of platelet function modulators or inhibitors.

12. The method of claim 1 wherein said method further includes mechanical, electromechanical, electronic, or pharmacologic of the coagulation cascade.

13. The method of claim 1 wherein one or more surrogate markers is utilized for monitoring total circulating platelet activity.

14. The method of claim 13 wherein total circulating platelet volume is the surrogate marker utilized for monitoring total circulating platelet activity.

15. The method of claim 13 wherein the treated patient is not having an acute vaso-occlusive crisis and platelet count is the surrogate marker utilized for monitoring total circulating platelet activity.

16. The method of claim 13 wherein the method of treating the patient is non-pharmacologic and platelet count is the surrogate marker utilized for monitoring total circulating platelet activity.

17. A method to reduce the incidence of and complications from peri-operative and post-operative thrombosis, to increase the efficiency of blood scavenging, or to reduce the complications of blood scavenging, prior to, during, or immediately after cardiovascular bypass surgery, coronary bypass surgery, vascular surgery or intra-cranial surgery comprising reducing the total circulating platelet activity below normal levels without a transient increase in the total circulating platelet activity, or a transient or permanent increase in the total number of platelets, activated platelets, immature platelets or platelet precursor cells in the peripheral circulation; wherein said method is applied prior to, during, or immediately after said surgery procedure.

18. A method to contain the damage done by activated-platelets and thus reduce the incidence of or treat the cardiac and vascular pathology that arises in dialysis patients comprising reducing the total circulating platelet activity below normal levels without a transient increase in the total circulating platelet activity, or a transient or permanent increase in the total number of platelets, activated platelets, immature platelets or platelet precursor cells in the peripheral circulation, wherein said method is applied prior to, during, or immediately after renal replacement therapy.

* * * * *